United States Patent
Arad et al.

(10) Patent No.: US 9,458,438 B2
(45) Date of Patent: Oct. 4, 2016

(54) SULFOTRANSFERASE OF A RED MICROALGA AND USES THEREOF

(75) Inventors: Shoshana Arad, Omer (IL); Lena Plesser, Beer Sheva (IL); Yaakov Weinstein, Omer (IL)

(73) Assignee: Ben Gurion University of the Negev Research and Development Authority, Beer Sheva (IL)

( * ) Notice: Subject to any disclaimer, the term of this patent is extended or adjusted under 35 U.S.C. 154(b) by 733 days.

(21) Appl. No.: 13/640,488

(22) PCT Filed: Apr. 11, 2011

(86) PCT No.: PCT/IL2011/000299
§ 371 (c)(1),
(2), (4) Date: Feb. 28, 2013

(87) PCT Pub. No.: WO2011/128895
PCT Pub. Date: Oct. 20, 2011

(65) Prior Publication Data
US 2013/0180012 A1    Jul. 11, 2013

Related U.S. Application Data

(60) Provisional application No. 61/322,923, filed on Apr. 12, 2010.

(51) Int. Cl.
| | | |
|---|---|---|
| *C12N 9/10* | (2006.01) | |
| *C12N 15/82* | (2006.01) | |
| *C12P 11/00* | (2006.01) | |
| *C07K 14/405* | (2006.01) | |
| *C12P 19/04* | (2006.01) | |

(52) U.S. Cl.
CPC ............. *C12N 9/13* (2013.01); *C07K 14/405* (2013.01); *C12N 9/10* (2013.01); *C12P 11/00* (2013.01); *C12P 19/04* (2013.01); *C12N 15/8243* (2013.01); *Y02P 20/52* (2015.11)

(58) Field of Classification Search
CPC ....................................................... C12N 9/10
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubinstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands et al. |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |
| 5,464,764 A | 11/1995 | Capecchi et al. |
| 5,487,992 A | 1/1996 | Capecchi et al. |
| 5,932,447 A | 8/1999 | Siegall |
| 8,936,930 B2 * | 1/2015 | Arad et al. ................. 435/257.2 |
| 2004/0029132 A1 | 2/2004 | Yue et al. |
| 2004/0043447 A1* | 3/2004 | Saribas et al. ............... 435/69.1 |

FOREIGN PATENT DOCUMENTS

WO    WO 2006/013572 A2    2/2006

OTHER PUBLICATIONS

Suter et al. (Adenosine 5'-Phosphosulfate Sulfotransferase and Adenosine 5'-Phosphosulfate Reductase Are Identical Enzymes, 275 J Bio Chem 930-936 (2000)).*
Suter et al. 2000. Adenosine 5-Phosphosulfate Sulfotransferase and Adenosine 5-Phosphosulfate reductase are identical enzymes. The journal of biological chemistry 275920: 930-936.*
Kanno et al. 1996. Adenosine 5'-phosphosulfate sulfotransferase from the marine macroalga Porphyra yezoensis Ueda (Rhodophyta): stabilization, purification, and properties. Planta 198: 440-446.*
Hernandez-Sebastia and Varin. 2008. Sulfotransferases from Plants, Algae and Phototrophic Bacteria. In Advances in Photosynthesis and Respiration vol. 27. Eds: Hell, Dahl, Knaff and Leustek. Springer, Dordrecht, The Netherlands.*
Shrestha and Arad. A glycoprotein noncovanlently associated with cell-wall polysaccharide of the red microalga *Porphyridium* sp (Rhodophyta). J. Phycol 40: 568-580.*
Shental-Bechor and Levy. 2008. Effect of glycosylation on protein folding: A close look at thermodynamic stabilization. PNAS 105: 8256-8261.*
Sharma et al. 2009. A simple and efficient Agrobacterium-mediated procedure for transformation of tomato. J. Siosci 34: 423-433.*
Boyen et al. "Nucleotide sequence of the cox3 gene from *Chondrus crispus*: evidence that UGA encodes tryptophan and evolutionary implications", Nucl. Acids Res. (1994) 22 (8): 1400-1403 doi:10.1093/nar/22.8.1400.
Brogli et al. "Light-regulated expression of a pea ribulose-1,5-bisphosphate carboxylase small subunit gene in transformed plant cells", (1984) Science 224:838-843.

(Continued)

*Primary Examiner* — Anne Kubelik
*Assistant Examiner* — Karen Redden
(74) *Attorney, Agent, or Firm* — Mark S. Cohen; Pearl Cohen Zedek Latzer Baratz LLP

(57) ABSTRACT

An isolated protein which is at least partially encoded by a polynucleotide sequence encoding a novel sulfotransferase is provided together with a composition which includes the isolated protein. A transgenic organism transformed by a polynucleotide encoding a protein which is at least partially encoded by a novel sulfotransferase is also provided. The invention also includes a process for in-vivo and in-vitro making a sulfated polysaccharide from an unsulfated polysaccharide or increasing the sulfur content of an already sulfated polysaccharide.

11 Claims, 9 Drawing Sheets

(56) References Cited

OTHER PUBLICATIONS

Brunold et al. "Studies of Sulfate Utilization of Algae: 15. Enzymes of Assijmilatory Sulfate Reduction in Euglena and their Cellular Locatlization", Plant Physiology, vol. 57, No. 3, Mar. 1, 1976, pp. 430-436.
Chapman et al. "Viral RNA silencing suppressors inhibit the microRNA pathway at an intermediate step", Genes & Development 18:1179-1186 , by Cold Spring Harbor Laboratory Press, 2004.
Chen et al. "Enzymatic redesigning of biologically active heparan sulfate", J Biol Chem, Dec. 30, 2005, vol. 280, No. 52, pp. 42817-42825.
Cheng et al. "Production of fertile transgenic peanut (*Arachis hypogaea* L.) plants using Agrobacterium tumefaciens", Plant Cell Rep. 15:653657 (1996).
Christou et al. "Stable Transformation of Soybean Callus by DNA-Coated Gold Particles", Plant Physiol. 87:671-674 (1988).
Coruzzi et al. "Tissue-specific and light-regulated expression of a pea nuclear gene encoding the small subunit of ribulose-1,5-bisphosphate carboxylase", (1984) EMBO J. 3:1671-1680.
Database UniProt (online), EBI Accession No. UNIPROT:B2GV63, Jun. 10, 2008, "SubName: Full=Carbohydrate (N-acetylgalactosamine 4-0) sulfotransferase 14; SubName: Full=Protein Chst14; SubName: Full=RCG26y700;", EB.
Gardella et al. "Expression of Human Parathyroid Hormone-( I-84) in *Escherichia coli* as a Factor X-cleavable Fusion Protein", J. Biol. Chem. 265:15854-15859 (1990).
Goff et al. "Transactivation of anthocyanin biosynthetic genes following transfer of B regulatory genes into maize tissues", EMBO J. 9:2517-2522 (1990).
Grant et al. "Transformation of peas (*Pisum sativum* L.) using immature cotyledons", Plant Cell Rep. 15:254-258, (1995).
Gurley et al. "Upstream Sequences Required for Efficient Expression of a Soybean Heat Shock Genet", (1986) Mol. Cell. Biol. 6:559-565.
Hattori et al. "The Viviparous-1 gene and abscisic acid activate the CI regulatory gene for anthocyanin biosynthesis during seed maturation in maize", Genes Dev. 6:609-618 (1992).
Hernandez-Sebastia et al. "Sulfotransferases from plants, algae and phototrophic bacteria", Jan. 1, 2008, Sulfur Metabolism in Phototrophic Organisms (Book Series: Advance in Photosynthesis and Respiration), Springer, pp. 111-130.
Honke et al. "Paranodal junction formation and spermatogenesis require sulfoglycolipids", PNAS Apr. 2, 2002 vol. 99 No. 7 4227-4232.
International Search Report for PCT Application No. PCT-IL 11/00299 dated Oct. 20, 2011.
Kang et al.; "A Role for Uric Acid in the Progression of Renal Disease", JASN Dec. 1, 2002 vol. 13 No. 12, 2888-2897.
Lidholt et al. "Substrate specificities of glycosyltransferaes involved in formation of heparin precursor and *E. coli* K5 capsular polysaccharides", Carbohydr Res, Mar. 4, 1994, vol. 255, pp. 87-101.
Marcotte et al. "Regulation of a wheat promoter by abscisic acid in rice protoplasts", Nature 335:454-457 (1988).
McCarthy et al. "Molecular Analysis of viíviparous-I: An Abscisic Acid Insensitive Mutant of Maize", Plant Cell 1:523-532 (1989).
McCarty et al. "The Viviparous-I Developmental Gene of Maize Encodes a Novel Transcriptional Activator", Cell 66:895-905 (1991).
McKently et al. "Agrobacterium-mediated transformation of peanut (*Arachis hypogaea* L.) embryo axes and the development of transgenic plants", Plant Cell Rep. 14:699-703 (1995).
Myette et al. "Expression in *Escherichia coli*, purification and kinetic characterization of human heparan sulfate 3-O-sulfotransferase-1", Biochem Biophys Res Comm, Feb. 1, 2002, vol. 290, No. 4, pp. 1206-1213.
Negishi et al. "Somatic-cell mutation induced by UVA and monochromatic UV radiation in repair-proficient and -deficient *Drosophila melanogaster*", 2001, Photochem. Photobiol. 73(5): 493-498.
Patwary et al. "Application of Rapd Markers in an Examination of Heterosis *Ingelidium Vagum* (*Rhodophyta*)", Journal of Phycology, vol. 30, Issue 1, pp. 91-97, Feb. 1994.
Ramus et al. "Incorporation of sulfate into the capsular polysaccharide of the red alga *Porphyridium*", J Cell Biol, Aug. 1972, vol. 54, No. 2, pp. 399-407.
Schmidt et al. "A Factor Dependent Sulfo Transferase Specific for 3 Phospho Adenosine 5 Phospho Sulfate in the Cyanbacterium Synechococcus 6301", Plant, Springer Verlag, DE, vol. 140, No. 3, Jan. 1, 1978, pp. 239-244.
Shrestha et al. "Role of $CD8^+$T Cells in Control of West Nile Virus Infection", Journal of Virology, Aug. 2004, p. 8312-8321.
Supplementary European Serach Report for European Application No. 11768559 dated Oct. 29, 2013.
Takamatsu et al. "Expression of bacterial chloramphenicol acetyltransferase gene in tobacco plants mediated by TMV-RNA", (1987) EMBO J. 6:307-311.
Wlad et al. "Biosynthesis of Heparin", The Journalo of Biological Chemistry, vol. 269, No. 40, pp. 24538-24541, Oct. 7, 1994.

\* cited by examiner

```
[SEQ ID NO 2]    1  atgtcgggagatgggatgcgagcggtgacggttcgccgacccgcgccgggcttggttggg    60
[SEQ ID NO 1]       M  S  G  D  G  M  R  A  V  T  V  R  R  P  A  P  G  L  V  G
                61  cgaatctggcgcggctagggcacccagtcgtgtcgcttgcgagcgtgttctgcgcgttg   120
                    R  I  W  R  G  L  G  H  P  V  V  S  L  A  S  V  F  C  A  L
               121  tattgtgtcgtgggcgtgtactatgccgagcgcaggaagggcgcggcttcgaagaagcg   180
                    Y  C  V  V  G  V  Y  Y  A  E  R  R  E  G  R  G  F  E  E  A
               181  ccgcagccgcgtgcgcggcggaaaaatgatctggcgcagcagccctagtggctctggac   240
                    P  Q  P  R  A  R  R  K  N  D  L  G  A  A  A  L  V  A  L  D
               241  ggctggatgtacgcaaatgagtcgactgtcagtcactgtcggtaatgcgtgacatgcgg   300
                    G  W  M  Y  A  N  E  S  T  L  Q  S  L  S  V  M  R  D  M  R
               301  aacgacgctgtggccgagagatgaatatatcgcgcaattgcgcgcagtcaaagacgagctc   360
                    N  D  A  V  A  R  D  E  Y  I  A  Q  L  R  A  V  K  D  E  L
               361  ggtgcttcgcgcttagccgccagagaggaaatggtcccgtctgctttgattccggagaat   420
                    G  A  S  R  L  A  A  R  E  E  M  V  P  S  A  L  I  P  E  N
               421  agcgtggatgtggaggtcatgatgcagcactcctttgccaaacggctcattgtttcgcaa   480
                    S  V  D  V  E  V  M  M  Q  H  S  F  A  K  R  L  I  V  S  Q
               481  cgcctgcgcgcgtctactgtccgataccgaaagtggctagcacaaattcaaacgcctg   540
                    R  L  R  A  V  Y  C  P  I  P  K  V  A  S  T  N  F  K  R  L
               541  atacgcaagtttgaaggctttagcgatcaccagaaccttacacgtgcacactcgagcgac   600
                    I  R  K  F  E  G  F  S  D  H  Q  N  L  T  R  A  H  S  S  D
               601  tctggccttgtgcgactttcggagctcgcgccggaattggctcggcaaatactcgaggac   660
                    S  G  L  V  R  L  S  E  L  A  P  E  L  A  R  Q  I  L  E  D
               661  cgcacgtacctcaaattcgtgtcgtgcgcgagccctactcgcgcgccctcagctgctac   720
                    R  T  Y  L  K  F  V  V  R  E  P  Y  S  R  A  L  S  C  Y
               721  ttgaacaagttccacacgcgacaaattagcggccctgagtttcggcgcttccttggccag   780
                    L  N  K  F  H  T  R  Q  I  S  G  P  E  F  R  R  F  L  G  Q
               781  ctggtcggctggaaatacataggcgacgccgaagtcaccgaggcagaccgccgacattt   840
                    L  V  G  W  K  Y  I  G  D  A  E  V  T  E  A  D  R  P  T  F
               841  gcgcggtttgtgaacgccatttggaagcaactacccgcgcagatgaacgagcactgggcg   900
                    A  R  F  V  N  A  I  W  K  Q  L  P  A  Q  M  N  E  H  W  A
               901  atccagagcgttttgtgcgggataggcgtgatcccgtatgactttgtggggcgcttcgag   960
                    I  Q  S  V  L  C  G  I  G  V  I  P  Y  D  F  V  G  R  F  E
               961  gagctgcctgagcatgcgctgctcatcctgcgcgctctgggaaagagtgccgagtcgttt  1020
                    E  L  P  E  H  A  L  L  I  L  R  A  L  G  K  S  A  E  S  F
              1021  ccgagtccatctgaaattggattcctcagcaccgaggccaacacgcagctcgatgcgttc  1080
                    P  S  P  S  E  I  G  F  L  S  T  E  A  N  T  Q  L  D  A  F
              1081  tacacgccggctctacgcagcagcgtgcgcgaaatctaccacgcggactttaatttactc  1140
                    Y  T  P  A  L  R  S  S  V  R  E  I  Y  H  A  D  F  N  L  L
              1141  gagtacgcaatctag                                              1155
                    E  Y  A  I  *
```

```
ST(P.sp.)       AIQSVRGIGVPFIDEICGPERALLRAIGKSAES-FESPSEIGFLSRANTL    357
D4ST(Mus musculus)    MPYYHIQPCAEIDECSEREADNQIEWRAPPHVRFARQAWYRPAPESLY    338
D4ST(Homo sapiens)    MPYYHIQPCAEIDECSEREADNQIEWRAPPHVRFARQAWYRPAPESLY    338
D4ST(Danio rerio)     MPIYNIQPCAEVDECSEREDSDSYLERGAPQHVRFERQTWYNPVKETLY    329
                                                    IV ST(P.sp.)       DAFYTE-ARSSRETRHADNEEAA------ 384
```

```
D4ST(Mus musculus)    HLCNVPRALQDLPKYILDESLAYPPNVTKEACHQ  376
D4ST(Homo sapiens)    HLCSAPRALQDLPKYILDESLAYPPNVTKEACQQ  376
D4ST(Danio rerio)     YLCTVPQKLKELPKYILDESLGYPPNTITEYCRH  367
                                              V
```

SULFOTRANSFERASE OF A RED MICROALGA AND USES THEREOF

CROSS-REFERENCE TO RELATED APPLICATIONS

This application is a National Phase Application of PCT International Application No. PCT/IL2011/000299, International Filing Date Apr. 11, 2011, which claims the benefit of U.S. Provisional Patent Application No. 61/322,923, filed Apr. 12, 2010, which are hereby incorporated by reference in their entirety.

FIELD OF INVENTION

This invention is directed to, inter alia, a protein having a sulfotransferase activity, isolated DNA molecules encoding the same, and methods of making and utilizing the same.

BACKGROUND OF THE INVENTION

Sulfation is common to a wide variety of organisms, from bacteria to eukaryotes, and it functions in a wide range of biological activities in the cell, i.e., cell-cell communication, cell growth, development, and protection. Sulfated polysaccharides exist in animals and in algae but not in terrestrial plants.

In nature, sulfation processes involve sulfotransferases (STs), a group of enzymes that catalyze the transfer of a sulfate group from the universal donor 3'-phosphoadenosine 5'-phosphosulfate (PAPS) to a variety of molecules—from low-molecular-weight hormones and xenobiotics to high-molecular-weight polysaccharides and proteins (Honke and Taniguchi, 2002).

STs are divided into two classes, cytosolic and membrane-associated. By virtue of their greater abundance in the cells and the ease with which they can be purified and assayed, cytosolic STs have been more thoroughly studied. Cytosolic STs catalyze the sulfation of small, hydrophobic molecules such as phenols and steroids, whereas the substrates of membrane-associated STs are hydrophilic polysaccharides, and protein. In addition, cytosolic STs can sulfate a wider variety of substrates than the more specific membrane-associated STs, which participate in biological processes such as molecular recognition, signal transduction and viral entry to the cell.

Most members of the ST family have similar structures. The PAPS-binding region is conserved at the amino acid level and contains the following structural motifs: a 5'-phosphosulfate-binding (5'-PSB) loop, a 3'-phosphate-binding (3'-PB) loop, and a β-strand-loop-α-helix (Chapman et al., 2004; Negishi et al., 2001). The largest variation among STs is found, as expected, in the substrate-binding region.

Most of what is known about ST enzymes is based on cytosolic STs, while the information of membrane-associated ST remains limited. Existing knowledge about membrane-associated STs comes mainly from animals, and so far no report has been published on STs from terrestrial plants or algae.

The cells of the red microalga *Porphyridium* sp. are encapsulated within a viscous sulfated polysaccharide, the external part of which dissolves into the growth medium. A complex heteropolymer (molecular mass $3-5 \times 10^6$ Da), this polysaccharide comprises about 10 monosaccharides, including the major sugars xylose, glucose, and galactose and the minor sugars mannose and methylated monosugars. The presence of glucuronic acid and sulfur esters, which constitute 3% of the molecule, make it anionic. This unique complex contains a non-covalently bound, 66-kDa glycoprotein that was identified as the main protein in the cell wall of *Porphyridium* sp. (Shrestha et al., 2004).

Sulfated polysaccharides play important roles in many biological processes. For example, the sulfated Lea tetra- and pentasaccharides are potent E-selectin inhibitors and sialyl Lewis x with a sulfate group at the 6-position of galactose is a ligand for L-selectin. These sulfated sugars play important roles, among others, in cell adhesion in response to inflammatory reactions. The sulfation of hydroxysteroids provides hydrophilic forms for excretion. Many glycosaminoglycans [GAGs] are sulfated and are involved in numerous cellular functions.

SUMMARY OF THE INVENTION

In one embodiment, the present invention provides an isolated protein comprising, an amino acid sequence set forth in SEQ ID NO: 1 (the putative membrane ST provided in FIG. 1).

In another embodiment, the present invention further provides an isolated polynucleotide comprising a coding portion encoding a protein comprising, an amino acid sequence set forth in SEQ ID NO: 1.

In another embodiment, the present invention further provides a method of producing a sulfated polysaccharide in a cell comprising the step of transforming a cell with a polynucleotide comprising a coding portion encoding a protein comprising, an amino acid sequence set forth in SEQ ID NO: 1, thereby producing a sulfated polysaccharide in a cell.

In another embodiment, the present invention further provides a method of producing a sulfated polysaccharide comprising the step of contacting a polysaccharide, a protein comprising an amino acid sequence set forth in SEQ ID NO: 1, and a sulfate group, thereby producing a sulfated polysaccharide.

In another embodiment, the present invention further provides an antibody that specifically binds to an isolated protein comprising, an amino acid sequence set forth in SEQ ID NO: 1.

In another embodiment, the present invention further provides a method of increasing a sulfur percentage in a polysaccharide in a cell, comprising the step of over expressing a polynucleotide sequence encoding a sulfotransferase in the cell, thereby increasing a sulfur percentage in a polysaccharide in a cell.

BRIEF DESCRIPTION OF THE DRAWINGS

FIG. 1. Depicts the nucleic acid (SEQ ID NO: 2) and amino acid (SEQ ID NO: 1) sequences of a putative membrane sulfotransferase (ST) from the red microalga *Porphyridium* sp.

FIG. 2. Is a comparison of the amino acid sequences of dermatan-4-O-sulfotransferase from *Mus musculus* (SEQ ID NO: 14), *Homo sapiens* (SEQ ID NO: 15), and *Danio rario* (SEQ ID NO: 16) to the ST of *Porphyridium* sp (SEQ ID NO: 1). Alignment was performed using the ClustalW algorithm. Introduced gaps are shown as hyphens, and aligned amino acids are boxed (black for identical residues and dark gray for similar residues). Putative binding sites for the 5'-phosphosulfonate group (5'-PSB) and 3'-phosphate group (3'-PB) of PAPS and three additional highly conserved domains (III, IV, and V) are indicated.

DETAILED DESCRIPTION OF THE INVENTION

Figure 3:
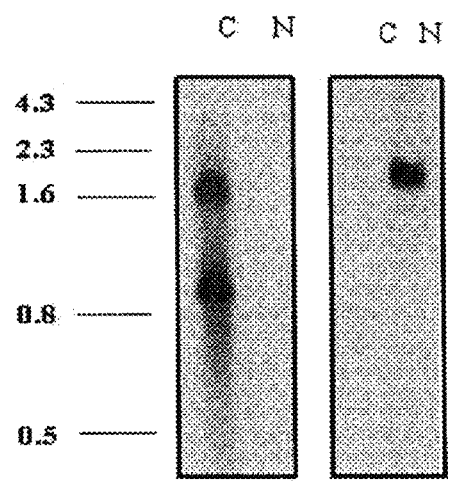
FIG. 3: Is a micrograph showing southern blot analysis. Total DNA was separated on a CsCl gradient into organellar (O) and nuclear (N) fractions. Fractionated DNA (10 g) digested by EcoRI was loaded in each line. The blots were hybridized with an AHAS probe that was encoded by the organellar genome (left blot) and with a sulfotransferase (ST) probe that hybridized exclusively with the nuclear genome (right blot). Molecular marker sizes are shown in kb on the far left.

In one embodiment, the present invention provides an isolated sulfotransferase. In another embodiment, the present invention provides that the isolated sulfotransferase is a microalga sulfotransferase. In another embodiment, the present invention provides that the isolated sulfotransferase is a red microalga sulfotransferase. In another embodiment, the present invention provides that the isolated sulfotransferase is a *Porphyridium* sp. (Rhodophyta) Sulfotransferase.

In another embodiment, the present invention provides a sulfotransferase comprising or consisting the amino acid sequence:

```
                                                            (SEQ ID NO: 1)
MSGDGMRAVTVRRPAPGLVGRIWRGLGHPVVSLASVFCALYCVVGVYYAERREGR

GFEEAPQPRARRKNDLGAAALVALDGWMYANESTLQSLSVMRDMRNDAVARDEYI

AQLRAVKDELGASRLAAREEMVPSALIPENSVDVEVMMQHSFAKRLIVSQRLRAVY

CPIPKVASTNFKRLIRKFEGFSDHQNLTRAHSSDSGLVRLSELAPELARQILEDRTYLK

FVVVREPYSRALSCYLNKFHTRQISGPEFRRFLGQLVGWKYIGDAEVTEADRPTFARF

VNAIWKQLPAQMNEHWAIQSVLCGIGVIPYDFVGRFEELPEHALLILRALGKSAESFP

SPSEIGFLSTEANTQLDAFYTPALRSSVREIYHADFNLLEYAI.
```

In another embodiment, the sulfotransferase of the present invention comprises an amino acid sequence that is at least 50% homologous to the amino acid sequence of SEQ ID NO: 1. In another embodiment, the sulfotransferase of the present invention comprises an amino acid sequence that is at least 60% homologous to the amino acid sequence of SEQ ID NO: 1. In another embodiment, the sulfotransferase of the present invention comprises an amino acid sequence that is at least 70% homologous to the amino acid sequence of SEQ ID NO: 1. In another embodiment, the sulfotransferase of the present invention comprises an amino acid sequence that is at least 80% homologous to the amino acid sequence of SEQ ID NO: 1. In another embodiment, the sulfotransferase of the present invention comprises an amino acid sequence that is at least 85% homologous to the amino acid sequence of SEQ ID NO: 1. In another embodiment, the sulfotransferase of the present invention comprises an amino acid sequence that is at least 90% homologous to the amino acid sequence of SEQ ID NO: 1. In another embodiment, the sulfotransferase of the present invention comprises an amino acid sequence that is at least 95% homologous to the amino acid sequence of SEQ ID NO: 1. In another embodiment, the sulfotransferase of the present invention comprises an amino acid sequence that is at least 99% homologous to the amino acid sequence of SEQ ID NO: 1.

In another embodiment, the sulfotransferase of the present invention comprises an amino acid sequence that is at least 50% identical to the amino acid sequence of SEQ ID NO: 1. In another embodiment, the sulfotransferase of the present invention comprises an amino acid sequence that is at least 60% identical to the amino acid sequence of SEQ ID NO: 1. In another embodiment, the sulfotransferase of the present invention comprises an amino acid sequence that is at least 70% identical to the amino acid sequence of SEQ ID NO: 1. In another embodiment, the sulfotransferase of the present invention comprises an amino acid sequence that is at least 80% identical to the amino acid sequence of SEQ ID NO: 1. In another embodiment, the sulfotransferase of the present invention comprises an amino acid sequence that is at least 85% identical to the amino acid sequence of SEQ ID NO: 1. In another embodiment, the sulfotransferase of the present invention comprises an amino acid sequence that is at least 90% identical to the amino acid sequence of SEQ ID NO: 1. In another embodiment, the sulfotransferase of the present invention comprises an amino acid sequence that is at least 95% identical to the amino acid sequence of SEQ ID NO: 1. In another embodiment, the sulfotransferase of the present invention comprises an amino acid sequence that is at least 99% identical to the amino acid sequence of SEQ ID NO: 1.

In another embodiment, the sulfotransferase as described herein comprises at least a portion of the amino acid shown in SEQ ID. NO: 1. In another embodiment, the sulfotransferase as described herein is a variant of SEQ ID. NO: 1. In another embodiment, the term "variant" in relation to a certain sequence means a protein or a polypeptide which is derived from the sequence through the insertion or deletion of one or more amino acid residues or the substitution of one or more amino acid residues with amino acid residues having similar properties, e.g., the replacement of a polar amino acid residue with another polar amino acid residue, or the replacement of a non-polar amino acid residue with another non-polar amino acid residue. In all cases, variants must have a ST function as defined herein.

In another embodiment, the sulfotransferase as described herein further comprises a leader peptide. In another embodiment, the leader peptide allows the polypeptide to be specifically located or targeted to a target organelle within the cell.

In another embodiment, the present invention provides an isolated sulfotransferase. In another embodiment, the present invention provides an isolated polypeptide comprising a functional sulfotransferase. In another embodiment, the present invention provides that the polypeptide has the function of a sulfotransferase.

In another embodiment, the present invention provides an isolated polynucleotide encoding the protein as described herein. In another embodiment, an isolated polynucleotide is an isolated DNA molecule. In another embodiment, an isolated polynucleotide is an isolated cDNA molecule. In another embodiment, the isolated polynucleotide comprises a sequence encoding the protein as described herein. In another embodiment, the isolated polynucleotide comprises a DNA sequence encoding a sulfotransferase as described herein. In another embodiment, the isolated polynucleotide comprises a DNA sequence encoding a polypeptide comprising a sulfotransferase activity. In another embodiment, the isolated polynucleotide comprises a DNA sequence encoding a polypeptide consisting a sulfotransferase activity.

In another embodiment, the isolated polynucleotide comprises a DNA sequence comprising or consisting the sequence:

```
(SEQ ID NO: 2)
atgtcgggagatgggatgcgagcggtgacggttcgccgacccgcgccgggcttggttgggcgaatctggcgcgggctagggcacc cagtcgtgtcgcttgcgagcgtgttctgcgcgttgtattgtgtcgtgggcgtgtactatgccgagcgcagggaagggcgcggcttcgaa gaagcgccgcagccgcgtgcgcggcggaaaaatgatctgggcgcagcagccctagtggctctggacggctggatgtacgcaaatg agtcgacgctgcagtcactgtcggtaatgcgtgacatgcggaacgacgctgtggcgagagatgaatatatcgcgcaattgcgcgcagt caaagacgagctcggtgcttcgcgcttagccgccagagaggaaatggtcccgtctgctttgattccggagaatagcgtggatgtggag gtcatgatgcagcactcctttgccaaacggctcattgtttcgcaacgcctgcgcgccgtctactgtccgataccgaaagtggctagcaca aatttcaaacgcctgatacgcaagtttgaagggtttagcgatcaccagaaccttacacgtgcacactcgagcgactctggccttgtgcga ctttcggagctcgcgccggaattggctcggcaaatactcgaggaccgcacgtacctcaaattcgtggtcgtgcgcgagccctactcgc gcgccctcagctgctacttgaacaagttccacacgcgacaaattagcggccctgagtttcggcgcttccttggccagctggtcggctgg aaatacataggcgacgccgaagtcaccgaggcagaccgcccgacatttgcgcggtttgtgaacgccatttggaagcaactacccgcg cagatgaacgagcactgggcgatccagagcgttttgtgcgggataggcgtgatcccgtatgactttgtggggcgcttcgaggagctgc ctgagcatgcgctgctcatcctgcgcgctctgggaaagagtgccgagtcgtttccgagtccatctgaaattggattcctcagcaccgag gccaacacgcagctcgatgcgttctacacgccggctctacgcagcagcgtgcgcgaaatctaccacgcggactttaatttactcgagta cgcaatctag.
```

In another embodiment, the isolated polynucleotide comprises a DNA sequence comprising or consisting the sequence:

(SEQ ID NO: 3)

```
atgacttgatcgcgcatcccgccctgctcgatcccagaatcgctgtcacttgcgttgccaccttcatcctgcaccattttcaccacgttggc
catcctgcttcgacgccacatagccaccccacgcgcgcactcgctccgcgcgacacgcgcgcgtccgcgatcaccttggatccagc
gaacacgcttcccgcccctacaaaacccatcgcaggtgccatcttttcactcctcgaagccacttttgccctccaaagcacactcacac
acgtcgcgactcaccacgactcgacgcacgcttgtcctcccccggctcatcccggcagctgccgcaatctcgccgacaaaatgtcggg
agatgggatgcgagcggtgacggttcgccgacccgcgccgggcttggttgggcgaatctggcgcgggctagggcacccagtcgtg
tcgcttgcgagcgtgttctgcgcgttgtattgtgtcgtgggcgtgtactatgccgagcgcagggaagggcgcggcttcgaagaagcgc
cgcagccgcgtgcgcggcggaaaaatgatctgggcgcagcagccctagtggctctggacggctggatgtacgcaaatgagtcgac
gctgcagtcactgtcggtaatgcgtgacatgcggaacgacgctgtggcgagagatgaatatatcgcgcaattgcgcgcagtcaaaga
cgagctcggtgcttcgcgcttagccgccagagaggaaatggtcccgtctgctttgattccggagaatagcgtggatgtggaggtcatg
atgcagcactcctttgccaaacggctcattgtttcgcaacgcctgcgcgccgtctactgtccgataccgaaagtggctagcacaaatttc
aaacgcctgatacgcaagtttgaagggtttagcgatcaccagaaccttacacgtgcacactcgagcgactctggccttgtgcgactttcg
gagctcgcgccggaattggctcggcaaatactcgaggaccgcacgtacctcaaattcgtggtcgtgcgcgagccctactcgcgcgcc
ctcagctgctacttgaacaagttccacacgcgacaaattagcggccctgagtttcggcgcttccttggccagctggtcggctggaaatac
ataggcgacgccgaagtcaccgaggcagaccgcccgacatttgcgcggtttgtgaacgccatttggaagcaactacccgcgcagatg
aacgagcactgggcgatccagagcgttttgtgcgggataggcgtgatcccgtatgactttgtggggcgcttcgaggagctgcctgagc
atgcgctgctcatcctgcgcgctctgggaaagagtgccgagtcgtttccgagtccatctgaaattggattcctcagcaccgaggccaac
acgcagctcgatgcgttctacacgccggctctacgcagcagcgtgcgcgaaatctaccacgcggactttaatttactcgagtacgcaat
ctag.
```

In another embodiment, the sulfotransferase of the present invention comprises a nucleic acid sequence that is at least 50% homologous to the nucleic acid sequence of SEQ ID NO: 2 or SEQ ID NO: 3. In another embodiment, the sulfotransferase of the present invention comprises a nucleic acid sequence that is at least 60% homologous to the nucleic acid sequence of SEQ ID NO: 2 or SEQ ID NO: 3. In another embodiment, the sulfotransferase of the present invention comprises a nucleic acid sequence that is at least 70% homologous to the nucleic acid sequence of SEQ ID NO: 2 or SEQ ID NO: 3. In another embodiment, the sulfotransferase of the present invention comprises a nucleic acid sequence that is at least 80% homologous to the nucleic acid sequence of SEQ ID NO: 2 or SEQ ID NO: 3. In another embodiment, the sulfotransferase of the present invention comprises a nucleic acid sequence that is at least 85% homologous to the nucleic acid sequence of SEQ ID NO: 2 or SEQ ID NO: 3. In another embodiment, the sulfotransferase of the present invention comprises a nucleic acid sequence that is at least 90% homologous to the nucleic acid sequence of SEQ ID NO: 2 or SEQ ID NO: 3. In another embodiment, the sulfotransferase of the present invention comprises a nucleic acid sequence that is at least 95% homologous to the nucleic acid sequence of SEQ ID NO: 2 or SEQ ID NO: 3. In another embodiment, the sulfotransferase of the present invention comprises a nucleic acid sequence that is at least 99% homologous to the nucleic acid sequence of SEQ ID NO: 2 or SEQ ID NO: 3.

In another embodiment, the sulfotransferase of the present invention comprises a nucleic acid sequence that is at least 50% identical to the nucleic acid sequence of SEQ ID NO: 2 or SEQ ID NO: 3. In another embodiment, the sulfotransferase of the present invention comprises a nucleic acid sequence that is at least 60% identical to the nucleic acid sequence of SEQ ID NO: 2 or SEQ ID NO: 3. In another embodiment, the sulfotransferase of the present invention comprises a nucleic acid that is at least 70% identical to the nucleic acid sequence of SEQ ID NO: 2 or SEQ ID NO: 3. In another embodiment, the sulfotransferase of the present invention comprises a nucleic acid sequence that is at least 80% identical to the nucleic acid sequence of SEQ ID NO: 2 or SEQ ID NO: 3. In another embodiment, the sulfotransferase of the present invention comprises a nucleic acid sequence that is at least 85% identical to the nucleic acid sequence of SEQ ID NO: 2 or SEQ ID NO: 3. In another embodiment, the sulfotransferase of the present invention comprises a nucleic acid sequence that is at least 90% identical to the nucleic acid sequence of SEQ ID NO: 2 or SEQ ID NO: 3. In another embodiment, the sulfotransferase of the present invention comprises a nucleic acid sequence that is at least 95% identical to the nucleic acid sequence of SEQ ID NO: 2 or SEQ ID NO: 3. In another embodiment, the sulfotransferase of the present invention comprises a nucleic acid sequence that is at least 99% identical to the nucleic acid sequence of SEQ ID NO: 2 or SEQ ID NO: 3.

In another embodiment, the present invention comprises a sulfotransferase or a nucleic acid molecule encoding the same combined with additional proteins and/or enzymes and/or substrates that are involved in the biosynthesis of sulfated polysaccharides. In another embodiment, the present invention comprises a sulfotransferase or a nucleic acid molecule encoding the same combined with additional proteins and/or enzymes and/or substrates that are involved in the biosynthesis of algal sulfated polysaccharides. In another embodiment, the present invention comprises a sulfotransferase or a nucleic acid molecule encoding the same combined with additional proteins and/or enzymes and/or substrates that are involved in the biosynthesis of red microalgal sulfated polysaccharides.

In another embodiment, polysaccharides are plant polysaccharides. In another embodiment, polysaccharides are algal polysaccharides. In another embodiment, polysaccharides are red microalga polysaccharides. In another embodiment, polysaccharides are bacterial polysaccharides. In another embodiment, polysaccharides are polysaccharides produced in or by animal cell. In another embodiment, polysaccharides are polysaccharides produced in or by marine organisms. In another embodiment, polysaccharides are polysaccharides produced in or by fresh water organisms. In another embodiment, polysaccharides are polysaccharides produced by the red microalga *Porphyridium* sp. In another embodiment, a polysaccharide as described herein is the substrate for the sulfotransferase as described herein.

In another embodiment, the polysaccharide is an O-desulfated algal polysaccharide. In another embodiment, the polysaccharide is a partially sulfated polysaccharide. In another embodiment, the polysaccharide is a partially sulfated algal polysaccharide. In another embodiment, a partially sulfated polysaccharide is a polysaccharide comprising at least one sulfate group that can be further sulfated. In another embodiment, a sulfated polysaccharide is carrageenan. In another embodiment, a sulfated polysaccharide is fucoidan. In another embodiment, a desulfated polysaccharide is the substrate for the sulfotransferase as described herein. In another embodiment, an algal desulfated polysaccharide is the substrate for the sulfotransferase as described herein. In another embodiment, a red microalgal desulfated polysaccharide is the substrate for the sulfotransferase as described herein. In another embodiment, the product of the sulfotransferase as described herein is carrageenan. In another embodiment, the product of the sulfotransferase as described herein is fucoidan. In another embodiment, the product of the sulfotransferase as described herein is alginate. In another embodiment, the product of the sulfotransferase as described herein is cellulose.

In another embodiment, the present invention comprises a composition comprising a sulfotransferase as described herein or a nucleic acid molecule encoding the same. In another embodiment, the present invention comprises a composition comprising a sulfated polysaccharide produced by a sulfotransferase as described herein. In another embodiment, the present invention comprises a composition comprising a sulfated polysaccharide produced by a transgenic or transformed organism comprising a polynucleotide molecule encoding the sulfotransferase as described herein. In another embodiment, the present invention comprises a composition comprising a sulfotransferase as described herein or a nucleic acid molecule encoding the same combined with additional proteins and/or enzymes and/or substrates that are involved in the biosynthesis of sulfated polysaccharides. In another embodiment, the present invention comprises a composition comprising a cell transfected or transformed by a nucleic acid molecule encoding a sulfotransferase as described herein. In another embodiment, the cell is a prokaryotic cell. In another embodiment, the cell is a eukaryotic cell. In another embodiment, the cell is a plant cell. In another embodiment, the cell is an algal cell. In another embodiment, the cell is a red microalga cell.

In another embodiment, provided herein a transgenic organism transformed by a polynucleotide of the invention. In another embodiment, the organism is a plant. In another embodiment, the organism is a seed. In another embodiment, the organism is an alga. In another embodiment, the organism is a microalga. In another embodiment, the organism is a red microalga. In another embodiment, provided herein a seed or an offspring of a transgenic organism as described herein wherein the seed or offspring expresses a sulfotransferase as described herein.

In another embodiment, the present invention comprises a sulfotransferase transgenic plant or a sulfotransferase transformed bacteria. In another embodiment, the present invention comprises a sulfotransferase transgenic microalga or alga. In another embodiment, the present invention comprises a sulfotransferase transgenic plant or a sulfotransferase transformed bacteria combined with additional enzymes and/or substrates that are involved in the biosynthesis of sulfated polysaccharides.

In another embodiment, the present invention comprises a red microalga *Porphyridium* over expressing a sulfotransferase as described herein. In another embodiment, the present invention comprises a cell or an organism over-expressing a sulfotransferase. In another embodiment, the present invention comprises a cell or an organism over-expressing an endogenic or exogenic sulfotransferase. In another embodiment, the present invention provides that over-expression of a sulfotransferase results in hyper sulfated polysaccharides.

In another embodiment, a red microalga as described herein is transformed with a vector comprising a polynucleotide molecule encoding a sulfotransferase under the control of a constitutively active promoter. In another embodiment, a red microalga as described herein is transformed with a vector comprising a polynucleotide molecule encoding a self sulfotransferase under the control of a constitutively active promoter. In another embodiment, *Porphyridium* sp. is transformed with a vector comprising a polynucleotide molecule encoding a self sulfotransferase under the control of a constitutively active promoter. In another embodiment, *Porphyridium* sp. is transformed with a vector comprising the polynucleotide molecule of SEQ ID NO: 2 or SEQ ID NO: 3 under the control of a constitutively active promoter. In another embodiment, *Porphyridium* sp. is transformed with a vector comprising a polynucleotide molecule encoding the protein comprising or consisting the amino acid sequence SEQ ID NO: 1, under the control of a constitutively active promoter. In another embodiment, an alga or microalga as described is transformed according to the methods described in EP1789530 which is hereby incorporated herein by reference in its entirety. In another embodiment, the methods described in EP1789530 are used for the introduction of an endogenous sulfotransferase (such as the one encoded by SEQ ID NO: 2 or SEQ ID NO: 3) into competent red microalgae cells, thereby over-expressing sulfotransferase in the red microalgae. In another embodiment, over-expressing sulfotransferase in the red microalgae results in increased sulfation of polysaccharides.

In another embodiment, a vector is used according to the cell or organism utilized. In another embodiment, bacterial, plant, and animal cell vectors are readily available to one of average skill in the art. In another embodiment, vector control elements are used according to the cell, organism, or tissue utilized. In another embodiment, bacterial, plant, and animal cell vector control elements are readily available to one of average skill in the art. In another embodiment, vector control elements comprise origin of replication and a promoter.

In another embodiment, the present invention provides a composition comprising a vector comprising the polynucleotide as described herein. In another embodiment, the present invention provides a composition comprising a vector comprising a polynucleotide encoding a sulfotransferase as described herein. In another embodiment, the present invention provides a composition comprising a sulfotransferase, a polysaccharide and a sulfate donor.

In another embodiment, a sulfate donor is any sulfate donor known to one of skill in the art. In another embodiment, the sulfate donor is 3'-phosphoadenosine 5'-phosphosulfate (PAPS), cysteine, $SO_3$, $Na_2SO_4$, or any combination thereof.

In another embodiment, one of skill in the art is able to prepare a composition comprising a sulfotransferase as described herein. In another embodiment, one of skill in the art is able to prepare a composition comprising a polynucleotide as described herein. In another embodiment, one of skill in the art is able to prepare a composition comprising a combination of polynucleotides, plasmids, vectors etc. as described herein. In another embodiment, the present invention provides a composition comprising the sulfotransferase as described herein to be used in industrial applications for the manufacturing of sulfated polysaccharides. In another embodiment, a composition as described herein is a kit comprising the components for the in vitro manufacturing of sulfated polysaccharides. In another embodiment, a composition as described herein is a kit comprising the components for the in vivo manufacturing of sulfated polysaccharides.

In another embodiment, provided herein a method of producing a sulfated polysaccharide in a cell comprising the step of transforming a cell with a polynucleotide as described herein, thereby producing a sulfated polysaccharide in a cell. In another embodiment, the cell is a eukaryotic cell. In another embodiment, the cell is a plant cell. In another embodiment, the cell is an animal cell. In another embodiment, the cell is a prokaryotic cell. In another embodiment, the cell is a bacterial cell.

In another embodiment, provided herein a method of producing a sulfated polysaccharide comprising the step of contacting a polysaccharide, a sulfotransferase, and a sulfate group, thereby producing a sulfated polysaccharide. In another embodiment, provided herein a method of producing, in vitro, a sulfated polysaccharide comprising the step of contacting a polysaccharide, a sulfotransferase, and a sulfate group, thereby producing a sulfated polysaccharide. In another embodiment, provided herein a method of producing a sulfated polysaccharide comprising the step of contacting a partially sulfated polysaccharide, a sulfotransferase, and a sulfate group, thereby over sulfating a sulfated polysaccharide. In another embodiment, provided herein a method of producing a sulfated polysaccharide comprising the step of contacting a desulfated polysaccharide, a sulfotransferase, and a sulfate group, thereby producing a sulfated polysaccharide.

In another embodiment, provided herein a method for increasing a sulfur percentage in a polysaccharide in a cell, comprising the step of over expressing a polynucleotide sequence encoding a sulfotransferase in a cell, thereby increasing a sulfur percentage in a polysaccharide in a cell. In another embodiment, the cell is a red microalga cell or a prokaryotic cell. In another embodiment, the cell is a plant cell. In another embodiment, the cell is any cell. In another embodiment, the cell is any of the cells as described herein. In another embodiment, the cell is a plant cell. In another embodiment, the sulfotransferase is any known sulfotransferase. In another embodiment, the sulfotransferase is the sulfotransferase described herein. In another embodiment, methods of over-expressing a protein encoded by a vector such as a plasmid are known to one of average skill in the art.

In another embodiment, the method for increasing a sulfur percentage in a polysaccharide in a cell comprises the step of over expressing a polynucleotide sequence encoding a self sulfotransferase in a cell. In another embodiment, the method for increasing a sulfur percentage in a polysaccharide in a red microalga cell comprises the step of over expressing a polynucleotide sequence encoding a self sulfotransferase in a red microalga cell. In another embodiment, the method for increasing a sulfur percentage in a polysaccharide in *Porphyridium* sp. comprises the step of over expressing a polynucleotide sequence encoding *Porphyridium* sp. sulfotransferase in *Porphyridium* sp. In another embodiment, the method for increasing a sulfur percentage in a polysaccharide in *Porphyridium* sp. comprises the step of over expressing the polynucleotide sequence of SEQ ID NO: 2 or SEQ ID NO: 3 in *Porphyridium* sp.

In another embodiment, provided herein an antibody that specifically binds to the sulfotransferase of SEQ ID NO: 1. In another embodiment, provided herein polyclonal antibodies that specifically bind to the sulfotransferase of SEQ ID NO: 1. In another embodiment, provided herein a composition comprising the polyclonal antibodies, wherein at least one of the antibodies is an antibody that specifically binds to the sulfotransferase of SEQ ID NO: 1.

In another embodiment, algae as described herein are eukaryotic organisms. In another embodiment, algae as described herein are photoautotrophic. In another embodiment, algae as described herein are mixotrophic. In another embodiment, algae as described herein are unicellular. In another embodiment, algae as described herein are multicellular. In another embodiment, algae as described herein are Excavata algae. In another embodiment, algae as described herein are Rhizaria algae. In another embodiment, algae as described herein are Chromista algae. In another embodiment, algae as described herein are Alveolata algae.

In another embodiment, algae as described herein are red Algae. In another embodiment, red algae comprise chlorophyll masked by a red or purplish pigment. In another embodiment, red algae are important source of agar and carrageenan. In another embodiment, the alga is Rhodophyta. In another embodiment, the term plant as used herein comprises alga. In another embodiment, the term plant as used herein comprises red alga. In another embodiment, the sulfated products of the invention are used as food additives such as but not limited to carrageenans and/or agar.

In another embodiment, transforming a first alga with an algal gene derived from a second alga such as described herein results in enhanced sulfation. In another embodiment, transforming an alga with an algal gene derived from the same alga such as described herein results in enhanced sulfation. In another embodiment, transforming an alga with an algal gene derived from the same alga such as described herein, under the control of an expression inducing promoter such as but not limited to a constitutively active promoter, results in enhanced sulfation.

In another embodiment, provided herein a method of hyper-sulfating a polysaccharide in a cell, comprising over-expressing a sulfotransferase in the cell. In another embodiment, transformation and inducement of sulfotransferase expression results enhanced biosynthesis of sulfated polysaccharides. In another embodiment, transformation and inducement via an inducible promoter or a constitutively active promoter results in enhanced biosynthesis of sulfated polysaccharides. In another embodiment, transformation and inducement via an inducible promoter or a constitutively active promoter controlling a sulfotransferase results in enhanced biosynthesis of sulfated polysaccharides. In another embodiment, transformation and inducement via an inducible promoter or a constitutively active promoter controlling a sulfotransferase results in enhanced sulfation of a polysaccharide. In another embodiment, enhanced sulfation of a polysaccharide comprises an increase in the number of sulfate groups on a given polysaccharide that is a substrate to a given sulfotransferase. In another embodiment, enhanced sulfation of a polysaccharide comprises an increase in the number of sulfated polysaccharides that are substrates of a given sulfotransferase. In another embodiment, enhanced sulfation of a polysaccharide in red microalga *Porphyridium* sp. comprises transforming a red microalga *Porphyridium* sp. with a vector comprising a red microalga *Porphyridium* sp. sulfotransferase DNA sequence of the invention under the control of an inducible promoter or a constitutively active promoter. In another embodiment, enhanced sulfation of a polysaccharide in red microalga *Porphyridium* sp. comprises transforming a red microalga *Porphyridium* sp. with a plant vector comprising a red microalga *Porphyridium* sp. sulfotransferase DNA sequence of the invention under the control of an inducible plant promoter or a constitutively plant active promoter.

In another embodiment, a DNA sequence as described herein such as but not limited to SEQ ID NO: 1 is used to engineer a transgenic organism. In another embodiment, the DNA sequences comprise the sequences provided in SEQ ID NO: 1 or variants of these sequences due, for example, to base substitutions, deletions, and/or additions.

In another embodiment, the present invention provides an expression vector comprising the polynucleotide as described herein. In another embodiment, the present invention provides a combination of expression vectors each comprising a polynucleotide as described herein. In another embodiment, the present invention provides a plant specific expression vector comprising the polynucleotide as described herein. In another embodiment, the present invention provides an algal specific expression vector comprising the polynucleotide as described herein. In another embodiment, the present invention provides a cell comprising the expression vector/s as described herein. In another embodiment, the expression vector/s is contained within an *agrobacterium*. In another embodiment, a cell is a bacterial cell, an animal cell, plant cell or an algal cell.

In another embodiment, the present invention provides transformed bacteria, transgenic plant, a transgenic seed, or a transgenic alga transformed by a polynucleotide as described herein. In another embodiment, the present invention provides transformed bacteria, a transgenic plant, a transgenic seed, or a transgenic alga transformed by any combination of polynucleotides as described herein. In another embodiment, the present invention provides that the transgenic plant is a true-breeding for the polynucleotide/s as described herein. In another embodiment, the present invention provides a transgenic seed, produced by a transgenic plant transformed by the polynucleotide/s as described herein. In another embodiment, transformed bacteria, a transformed cell, a transgenic plant, a transgenic seed, or a transgenic alga as described herein produces sulfate enriched polysaccharides.

In another embodiment, the present invention provides that the methods as described herein can be utilized to de-novo sulfate unsulfated polysaccharides. In another embodiment, the present invention provides that the methods as described herein can be utilized for sulfating polysaccharides in cells or organisms that are not sulfated normally. In another embodiment, the present invention provides that the methods as described herein can be utilized for sulfating polysaccharides in plant cells or plant that are not sulfated normally. In another embodiment, the present invention provides that transforming a cell or an organism, transfecting a cell, or creating a transgenic organism in accordance to the invention results in sulfating polysaccharides that are were not sulfated naturally before. In another embodiment, the present invention provides that transforming a cell or an organism, transfecting a cell, or creating a transgenic organism in accordance to the invention results in increased or enhanced sulfation of polysaccharides that were less sulfated, naturally, before.

In another embodiment, the terms "enhanced sulfation", "over sulfation", "increased sulfation", "induced sulfation", "hyper sulfation", and "elevated sulfation", are used interchangeably. In another embodiment, "enhanced sulfation" is enhanced polysaccharide sulfation. In another embodiment, "enhanced sulfation" is enhanced protein sulfation.

In another embodiment, enhanced sulfation is the result of the introduction of a vector comprising a DNA molecule as described herein into a cell. In another embodiment, enhanced sulfation is the result of the introduction of a vector comprising a DNA molecule as described herein under the control of a promoter as described herein into a cell. In another embodiment, enhanced sulfation is the result of the introduction of a vector comprising a DNA molecule as described herein under the control of a promoter as described herein into a cell. In another embodiment, enhanced sulfation is the result of contacting a protein as described herein with a polysaccharide as described herein in the presence of a sulfate donor. In another embodiment, enhanced sulfation is the result of contacting a protein as described herein with a sulfated polysaccharide as described herein in the presence of a sulfate donor. In another embodiment, de-novo sulfation is the result of contacting a protein as described herein with an unsulfated polysaccharide as described herein in the presence of a sulfate donor.

In another embodiment, enhanced sulfation in a cell or an organism results in more polysaccharide molecules that are sulfated compared to the number of sulfated polysaccharide molecules present in a cell or an organism prior to the introduction of a DNA molecule as described herein. In another embodiment, enhanced sulfation in a cell or an organism results in increased number of sulfate groups on a polysaccharide molecule already sulfated (hyper sulfation) compared to the number of sulfate groups on a polysaccharide molecule in a cell or an organism prior to the introduction of a DNA molecule as described herein. In another embodiment, enhanced sulfation in a cell or an organism results in de novo sulfation of a polysaccharide molecule that was free of sulfate groups prior to the introduction of a DNA molecule as described herein.

In another embodiment, enhanced sulfation as described herein results in 5% increase in the number of sulfated polysaccharide molecules present in a cell. In another embodiment, enhanced sulfation as described herein results in 3-10% increase in the number of sulfated polysaccharide molecules present in a cell. In another embodiment, enhanced sulfation as described herein results in 7-20% increase in the number of sulfated polysaccharide molecules present in a cell. In another embodiment, enhanced sulfation as described herein results in 10-30% increase in the number of sulfated polysaccharide molecules present in a cell. In another embodiment, enhanced sulfation as described herein results in 10-80% increase in the number of sulfated polysaccharide molecules present in a cell. In another embodiment, enhanced sulfation as described herein results in 10-100% increase in the number of sulfated polysaccharide molecules present in a cell. In another embodiment, enhanced sulfation as described herein results in 5-150% increase in the number of sulfated polysaccharide molecules present in a cell. In another embodiment, enhanced sulfation as described herein results in 5-500% increase in the number of sulfated polysaccharide molecules present in a cell. In another embodiment, enhanced sulfation as described herein results in 10-50% increase in the number of sulfated polysaccharide molecules present in a cell. In another embodiment, enhanced sulfation as described herein results in 10-80% increase in the number of sulfated polysaccharide molecules present in a cell. In another embodiment, enhanced sulfation as described herein results in 30-70% increase in the number of sulfated polysaccharide molecules present in a cell. In another embodiment, enhanced sulfation as described herein results in 20-40% increase in the number of sulfated polysaccharide molecules present in a cell. In another embodiment, enhanced sulfation as described herein results in 30-50% increase in the number of sulfated polysaccharide molecules present in a cell. In another embodiment, enhanced sulfation as described herein results in 30-40% increase in the number of sulfated polysaccharide molecules present in a cell.

In another embodiment, enhanced sulfation as described herein results in 5% increase in the number of sulfate groups on a polysaccharide molecule present in a cell. In another embodiment, enhanced sulfation as described herein results in 3-10% increase in the number of sulfate groups on a polysaccharide molecule present in a cell. In another embodiment, enhanced sulfation as described herein results in 7-20% increase in the number of sulfate groups on a polysaccharide molecule present in a cell. In another embodiment, enhanced sulfation as described herein results in 10-30% increase in the number of sulfate groups on a polysaccharide molecule present in a cell. In another embodiment, enhanced sulfation as described herein results in 10-80% increase in the number of sulfate groups on a polysaccharide molecule present in a cell. In another embodiment, enhanced sulfation as described herein results in 10-100% increase in the number of sulfate groups on a polysaccharide molecule present in a cell. In another embodiment, enhanced sulfation as described herein results in 5-150% increase in the number of sulfate groups on a polysaccharide molecule present in a cell. In another embodiment, enhanced sulfation as described herein results in 5-500% increase in the number of sulfate groups on a polysaccharide molecule present in a cell. In another embodiment, enhanced sulfation as described herein results in 10-50% increase in the number of sulfate groups on a polysaccharide molecule present in a cell. In another embodiment, enhanced sulfation as described herein results in 10-80% increase in the number of sulfate groups on a polysaccharide molecule present in a cell. In another embodiment, enhanced sulfation as described herein results in 30-70% increase in the number of sulfate groups on a polysaccharide molecule present in a cell. In another embodiment, enhanced sulfation as described herein results in 20-40% increase in the number of sulfate groups on a polysaccharide molecule present in a cell. In another embodiment, enhanced sulfation as described herein results in 30-50% increase in the number of sulfate groups on a polysaccharide molecule present in a cell. In another embodiment, enhanced sulfation as described herein results in 30-40% increase in the number of sulfate groups on a polysaccharide molecule present in a cell.

In another embodiment, provided herein a sulfotransferase gene cloned from a red microalga. In another embodiment, provided herein a sulfotransferase gene which displays 10-80% identity to mammalian dermatan-4-O-sulfotransferase. In another embodiment, provided herein a sulfotransferase gene which displays 30-90% identity to mammalian dermatan-4-O-sulfotransferase. In another embodiment, provided herein a sulfotransferase gene which displays 49% identity to mammalian dermatan-4-O-sulfotransferase.

In another embodiment, provided herein a sulfotransferase gene encoded by the nucleus (and not the chloroplast). In another embodiment, provided herein a sulfotransferase gene which is a membrane bound protein. In another embodiment, provided herein a sulfotransferase gene from *Porphyridium* sp. expressed in *Escherichia coli* BL21 (DE3) cells. In another embodiment, provided herein a sulfotransferase gene expressed from a prokaryotic expression vector. In another embodiment, provided herein a sulfotransferase gene expressed from a eukaryotic expression vector. In another embodiment, provided herein a sulfotransferase gene expressed from a pET32a prokaryotic expression vector.

In another embodiment, provided herein that the conditions for the enzymatic activity of the recombinant algal sulfotransferase comprises pH 5-9. In another embodiment, provided herein that the conditions for the enzymatic activity of the recombinant algal sulfotransferase comprises pH 6-8. In another embodiment, provided herein that the optimal conditions for the enzymatic activity of the recombinant algal sulfotransferase comprises pH 7. In another embodiment, provided herein that the optimal conditions for the enzymatic activity of the recombinant algal sulfotransferase comprises 36-38° C. In another embodiment, provided herein that the optimal conditions for the enzymatic activity of the recombinant algal sulfotransferase comprises 37° C. In another embodiment, provided herein that the optimal conditions for the enzymatic activity of the recombinant algal sulfotransferase comprises 1.917 pg/μl recombinant sulfotransferase, and 0.015 μg/μl desulfated polysaccharide as a substrate. In another embodiment, provided herein that the optimal conditions for the enzymatic activity of the recombinant algal sulfotransferase comprises reaction time of 5-15 minutes. In another embodiment, provided herein that the optimal conditions for the enzymatic activity of the recombinant algal sulfotransferase comprises reaction time of 6-10 minutes. In another embodiment, provided herein that the optimal conditions for the enzymatic activity of the recombinant algal sulfotransferase comprises reaction time of 8 min.

In another embodiment, provided herein a sulfotransferase protein of 385 amino acid residues with a molecular mass of 43 kDa and two potential N-linked glycosylation sites (FIG. 1). In another embodiment, provided herein a sulfotransferase protein comprising a hydrophobic segment comprising 22 amino acid residues in the NH$_2$-terminal region. In another embodiment, provided herein a sulfotransferase protein comprising a putative 5'-PSB site. In another embodiment, provided herein a sulfotransferase protein comprising three regions of the carboxyl terminal that are substrates binding sites. In another embodiment, provided herein a membrane located sulfotransferase protein (see FIG. 4).

In another embodiment, provided herein a sulfotransferase protein expressed in a bacteria. In another embodiment, provided herein a recombinant sulfotransferase protein. In another embodiment, provided herein a Porphyridium sp. sulfotransferase protein expressed in bacteria. In another embodiment, provided herein a sulfotransferase protein of 64.5 kDa (see FIG. 5). In another embodiment, provided herein a Porphyridium sp. sulfotransferase recombinant protein expressed in a bacteria of 64.5 kDa (see FIG. 5). In another embodiment, provided herein a Porphyridium sp. sulfotransferase recombinant protein having pH and temperature dependence as provided herein.

In another embodiment, the invention further provides an engineered organism, such as a transgenic plant. In another embodiment, the invention further provides an engineered organism, such as a transgenic seed. In another embodiment, the invention further provides an engineered organism, such as a transgenic alga. In another embodiment, the invention further provides an engineered organism, such as a transgenic animal. In another embodiment, an engineered organism is engineered to express a protein as described herein. In another embodiment, an engineered organism is engineered to highly express a protein as described herein. In another embodiment, an engineered organism is engineered to express elevated levels of the protein as described herein. In another embodiment, an engineered plant as described herein is used for manufacturing desired sulfated polysaccharides. In another embodiment, an engineered plant as described herein is used for manufacturing desired hyper sulfated polysaccharides.

In another embodiment, an engineered organism comprises a synthetic pathway for the production of a protein. In another embodiment, an engineered organism comprising a synthetic pathway for the production of the protein allows greater control over the production of sulfated polysaccharides.

In another embodiment, an engineered plant or seed comprises an oligonucleotide as described herein. In another embodiment, an engineered plant or seed produces a protein as described herein and comprises an oligonucleotide as described herein. In another embodiment, an engineered plant or seed produces proteins as described herein and comprises oligonucleotides as described herein.

In another embodiment, expression of the protein/s of the invention in plants or seed requires subcloning an ORF/s sequence encoding the protein/s into a plant expression vector, which may comprise a viral 35S promoter, and a Nos terminator. In another embodiment, a cassette or promoter/coding sequence/terminator is then be subcloned into the plant binary transformation vector, and the resulting plasmid introduced into Agrobacterium. In another embodiment, the Agrobacterium strain transforms the plant. In another embodiment, the Agrobacterium strain transforms the plant by the vacuum-infiltration of inflorescences, and the seeds harvested and plated onto selective media containing an antibiotic. In another embodiment, the plasmid confers resistance to an antibiotic, thus only transformed plant material will grow in the presence of an antibiotic. In another embodiment, resistant lines are identified and self-fertilized to produce homozygous material. In another embodiment, leaf material is analyzed for expression of the protein comprising ST activity. In another embodiment, leaf material is analyzed for expression of a combination of protein comprising ST activity. In another embodiment, transformation of a sulfotransferase as described herein is a nuclear transformation. In another embodiment, transformation of a sulfotransferase as described herein is organellar transformation. In another embodiment, transformation of a sulfotransferase as described herein is a chloroplast transformation. In another embodiment, transformation of a sulfotransferase as described herein is a mitochondrial transformation.

In some embodiments, "protein", "sulfotransferase", or "polypeptide" as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which have, in some embodiments, modifications rendering the polypeptides/proteins even more stable while in-vivo or more capable of penetrating into cells.

In some embodiments, modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

In some embodiments, polypeptide bonds (—CO—NH—) within the polypeptide are substituted. In some embodiments, the polypeptide bonds are substituted by N-methylated bonds (—N(CH3)-CO—). In some embodiments, the polypeptide bonds are substituted by ester bonds (—C(R)H—C—O—O—C(R)—N—). In some embodiments, the polypeptide bonds are substituted by ketomethylene bonds (—CO—CH2-). In some embodiments, the polypeptide bonds are substituted by α-aza bonds (—NH—N(R)—CO—), wherein R is any alkyl, e.g., methyl, carbo bonds (—CH2-NH—). In some embodiments, the polypeptide bonds are substituted by hydroxyethylene bonds (—CH(OH)—CH2-). In some embodiments, the polypeptide bonds are substituted by thioamide bonds (—CS—NH—). In some embodiments, the polypeptide bonds are substituted by olefinic double bonds (—CH=CH—). In some embodiments, the polypeptide bonds are substituted by retro amide bonds (—NH—CO—). In some embodiments, the polypeptide bonds are substituted by polypeptide derivatives (—N(R)—CH2-CO—), wherein R is the "normal" side chain, naturally presented on the carbon atom. In some embodiments, these modifications occur at any of the bonds along the polypeptide chain and even at several (2-3 bonds) at the same time.

In some embodiments, natural aromatic amino acids of the polypeptide such as Trp, Tyr and Phe, be substituted for synthetic non-natural acid such as Phenylglycine, TIC, naphthylelanine (Nol), ring-methylated derivatives of Phe, halogenated derivatives of Phe or o-methyl-Tyr. In some embodiments, the polypeptides of the present invention include one or more modified amino acid or one or more non-amino acid monomers (e.g., fatty acid, complex carbohydrates, etc.).

In one embodiment, "amino acid" or "amino acid" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acid.

In some embodiments, the polypeptides or proteins of the present invention are utilized in a soluble form. In some embodiments, the polypeptides or proteins of the present invention include one or more non-natural or natural polar amino acid, including but not limited to serine and threonine which are capable of increasing polypeptide or protein solubility due to their hydroxyl-containing side chain.

In some embodiments, the polypeptides or proteins of the present invention are utilized in a linear form, although it will be appreciated by one skilled in the art that in cases where cyclization does not severely interfere with polypeptide characteristics, cyclic forms of the polypeptide can also be utilized.

In some embodiments, the polypeptides or proteins of present invention are biochemically synthesized such as by using standard solid phase techniques. In some embodiments, these biochemical methods include exclusive solid phase synthesis, partial solid phase synthesis, fragment condensation, or classical solution synthesis. In some embodiments, these methods are used when the polypeptide is relatively short (about 5-15 kDa) and/or when it cannot be produced by recombinant techniques (i.e., not encoded by a nucleic acid sequence) and therefore involves different chemistry.

In some embodiments, solid phase polypeptide or protein synthesis procedures are well known to one skilled in the art and further described by John Morrow Stewart and Janis Dillaha Young, Solid Phase Polypeptide Syntheses (2nd Ed., Pierce Chemical Company, 1984). In some embodiments, synthetic polypeptides or proteins are purified by preparative high performance liquid chromatography [Creighton T. (1983) Proteins, structures and molecular principles. WH Freeman and Co. N.Y.], and the composition of which can be confirmed via amino acid sequencing by methods known to one skilled in the art.

In some embodiments, recombinant protein techniques are used to generate the polypeptides of the present invention. In some embodiments, recombinant protein techniques are used for generation of relatively long polypeptides (e.g., longer than 18-25 amino acid). In some embodiments, recombinant protein techniques are used for the generation of large amounts of the polypeptide of the present invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al, (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

In one embodiment, a polypeptide or protein of the present invention is synthesized using a polynucleotide encoding a polypeptide or protein of the present invention as described herein. In some embodiments, the polynucleotide encoding a polypeptide of the present invention is ligated into an expression vector, comprising a transcriptional control of a cis-regulatory sequence (e.g., promoter sequence). In some embodiments, the cis-regulatory sequence is suitable for directing constitutive expression of the polypeptide of the present invention. In some embodiments, the cis-regulatory sequence is suitable for directing tissue specific expression of the polypeptide of the present invention. In some embodiments, the cis-regulatory sequence is suitable for directing inducible expression of the polypeptide of the present invention. In another embodiment, a polypeptide is a protein comprising a ST activity as described herein.

In another embodiment, the polynucleotide comprises a genomic polynucleotide sequence. In another embodiment, the polynucleotide comprises a composite polynucleotide sequence.

In one embodiment, the phrase "a polynucleotide" refers to a single or double stranded nucleic acid sequence which be isolated and provided in the form of an RNA sequence, a complementary polynucleotide sequence (cDNA), a genomic polynucleotide sequence and/or a composite polynucleotide sequences (e.g., a combination of the above).

In one embodiment, "genomic polynucleotide sequence" refers to a sequence derived (isolated) from a chromosome and thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the polypeptide of the present invention, as well as some intronic sequences interposing there between. In one embodiment, the intronic sequences can be of any source, including of other genes, and typically will include conserved splicing signal sequences. In one embodiment, intronic sequences include cis acting expression regulatory elements.

In one embodiment, the polynucleotides of the present invention further comprise a signal sequence encoding a signal peptide for the secretion of the polypeptides of the present invention. In one embodiment, following expression, the signal peptides are cleaved from the precursor proteins resulting in the mature proteins.

In some embodiments, polynucleotides of the present invention are prepared using PCR techniques or any other method or procedure known to one skilled in the art. In some embodiments, the procedure involves the legation of two different DNA sequences (See, for example, "Current Protocols in Molecular Biology", eds. Ausubel et al., John Wiley & Sons, 1992).

In one embodiment, polynucleotides of the present invention are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhancers) and transcription and translation terminators (e.g., polyadenylation signals).

In one embodiment, a variety of prokaryotic or eukaryotic cells can be used as host-expression systems to express the polypeptides of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In some embodiments, non-bacterial expression systems are used (e.g., plant expression systems) to express the polypeptide of the present invention.

In one embodiment, yeast expression systems are used. In one embodiment, algae expression systems are used. In one embodiment, plant expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In another embodiment, expression in a host cell can be accomplished in a transient or a stable fashion. In another embodiment, a host cell is a cell as described herein. In another embodiment, transient expression is from introduced constructs which contain expression signals functional in the host cell, but which constructs do not replicate and rarely integrate in the host cell, or where the host cell is not proliferating. In another embodiment, transient expression also can be accomplished by inducing the activity of a regulatable promoter operably linked to the gene of interest.

In another embodiment, stable expression is achieved by introduction of a construct that integrates into the host genome. In another embodiment, stable expression comprises autonomously replication within the host cell. In another embodiment, stable expression of the polynucleotide of the invention is selected for through the use of a selectable marker located on or transfected with the expression construct, followed by selection for cells expressing the marker. In another embodiment, stable expression results from integration, the site of the construct's integration can occur randomly within the host genome or can be targeted through the use constructs containing regions of homology with the host genome sufficient to target recombination with the host locus. In another embodiment, constructs are targeted to an endogenous locus, all or some of the transcriptional and translational regulatory regions can be provided by the endogenous locus.

In another embodiment, an expression of a protein as described herein comprising sulfotransferase activity includes functional transcriptional and translational initiation and termination regions that are operably linked to the DNA encoding the protein comprising a sulfotransferase activity. In another embodiment, an expression of proteins as described herein comprising various sulfotransferase activities includes functional transcriptional and translational initiation and termination regions that are operably linked to the DNA encoding the proteins comprising sulfotransferase activity. In another embodiment, an expression of proteins as described herein comprising sulfotransferase activity includes functional transcriptional and translational initiation and termination regions that are operably linked to the DNA encoding the protein comprising a sulfotransferase activity. In another embodiment, transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. In another embodiment, expression in a plant tissue and/or plant part presents certain efficiencies, particularly where the tissue or part is one which is harvested early, such as seed, leaves, fruits, flowers, roots, etc. In another embodiment, expression can be targeted to that location in a plant by utilizing specific regulatory sequences that are known to one of skill in the art. In another embodiment, the expressed protein is an enzyme which produces a product which may be incorporated, either directly or upon further modifications, into a fluid fraction from the host plant. In another embodiment, expression of a protein of the invention, or antisense thereof, alters the levels of specific PUFAs, or derivatives thereof, found in plant parts and/or plant tissues. The sulfotransferase coding region, in some embodiments, may be expressed either by itself or with other genes, in order to produce cells, tissues, algae, and/or plant parts containing higher proportions of desired sulfated or hypersulfated polysaccharides. In another embodiment, the termination region is derived from the 3' region of the gene from which the initiation region was obtained or from a different gene. In another embodiment, the termination region usually is selected as a matter of convenience rather than because of any particular property.

In another embodiment, a plant or plant tissue is utilized as a host or host cell, respectively, for expression of the protein of the invention which may, in turn, be utilized in the production of polyunsaturated fatty acids. In another embodiment, desired PUFAS are expressed in seed. In another embodiment, methods of isolating seed oils are known in the art. In another embodiment, seed oil components are manipulated through the expression of the protein of the invention in order to provide seed oils that can be added to nutritional compositions, pharmaceutical compositions, animal feeds and cosmetics. In another embodiment, a vector which comprises a DNA sequence encoding the protein as described herein is linked to a promoter, and is introduced into the plant tissue or plant for a time and under conditions sufficient for expression of the protein.

In another embodiment, a vector as described herein comprises additional genes that encode other enzymes, involved in polysaccharide synthesis and/or modification. In another embodiment, the bacteria, plant tissue or plant produces the relevant substrate upon which the enzymes act or a vector encoding enzymes which produce such substrates may be introduced into the plant tissue, plant cell or plant. In another embodiment, a substrateis in contact with the bacteria, or is sprayed on plant tissues expressing the appropriate enzymes. In another embodiment, the invention is directed to a transgenic plant comprising the above-described vector, wherein expression of the nucleotide sequence of the vector results in production of a polyunsaturated fatty acid in, for example, the seeds of the transgenic plant.

In another embodiment, the regeneration, development, and cultivation of plants from single plant protoplast transformants or from various transformed explants is well known in the art (for example: Weissbach and Weissbach, In: Methods for Plant Molecular Biology, (Eds.), Academic Press, Inc. San Diego, Calif., (1988)). In another embodiment, regeneration and growth process comprises the steps of selection of transformed cells, culturing those individualized cells through the usual stages of embryonic development to through the rooted plantlet stage. In another embodiment, transgenic embryos and seeds are similarly regenerated. In another embodiment, resulting transgenic rooted shoots are thereafter planted in an appropriate plant growth medium such as soil. In another embodiment, regeneration and growth process of algae are known to one of skill in the art. In another embodiment, identification, selection, of transgenic algae are known to one of skill in the art.

In another embodiment, development or regeneration of plants containing an exogenous polynucleotide as described herein encodes a protein as described herein and is well known in the art. In another embodiment, development or regeneration of algae containing an exogenous polynucleotide as described herein encodes a protein as described herein and is well known in the art. In another embodiment, the regenerated plants are self-pollinated to provide homozygous transgenic plants. In another embodiment, pollen obtained from the regenerated plants is crossed to seed-grown plants of agronomically important lines. In another embodiment, pollen from plants of these important lines is used to pollinate regenerated plants. In another embodiment, a transgenic plant of the present invention containing a desired polypeptide is cultivated using methods well known to one skilled in the art.

In another embodiment, a variety of methods can be utilized for the regeneration of plants from plant tissue. In another embodiment, the method of regeneration will depend on the starting plant tissue and the particular plant species to be regenerated. In another embodiment, methods for transforming dicots, primarily by use of *Agrobacterium tumefaciens*, and obtaining transgenic plants are known in the art McCabe et al., Biol. Technology 6:923 (1988), Christou et al., Plant Physiol. 87:671-674 (1988)); Cheng et al., Plant Cell Rep. 15:653657 (1996), McKently et al., Plant Cell Rep. 14:699-703 (1995)); Grant et al., Plant Cell Rep. 15:254-258, (1995).

In another embodiment, transformation of monocotyledons using electroporation, particle bombardment, and *Agrobacterium* are known. In another embodiment, transformation and plant regeneration are well established in the art. In another embodiment, assays for gene expression based on the transient expression of cloned nucleic acid constructs have been developed by introducing the nucleic acid molecules into plant cells by polyethylene glycol treatment, electroporation, or particle bombardment (Marcotte et al., Nature 335:454-457 (1988); Marcotte et al., Plant Cell 1:523-532 (1989); McCarty et al., Cell 66:895-905 (1991); Hattori et al., Genes Dev. 6:609-618 (1992); Goff et al., EMBO J. 9:2517-2522 (1990)).

In another embodiment, transient expression systems are used to functionally dissect the oligonucleotides constructs. In another embodiment, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, N.Y. (1997)).

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric polypeptide.

In some embodiments, expression vectors containing regulatory elements from eukaryotic viruses such as retroviruses are used by the present invention. In some embodiments, recombinant viral vectors are useful for in vivo expression of the polypeptides of the present invention since they offer advantages such as lateral infection and targeting specificity. In one embodiment, lateral infection is inherent in the life cycle of, for example, retrovirus, and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In one embodiment, plant expression vectors are used. In one embodiment, the expression of a polypeptide coding sequence is driven by a number of promoters. In some embodiments, viral promoters such as the $^{35}$S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide or protein), the expression construct of the present invention can also include sequences engineered to optimize stability, production, purification, yield or activity of the expressed polypeptide or protein.

In some embodiments, transformed cells are cultured under effective conditions, which allow for the expression of high amounts of recombinant polypeptide or protein. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide or protein of the present invention. In some embodiments, a. medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant polypeptides or proteins of the present invention either remain within the recombinant cell, secreted into the fermentation medium, secreted into a space between two cellular membranes, or retained on the outer surface of a cell or viral membrane.

In one embodiment, following a predetermined time in culture, recovery of the recombinant polypeptide or protein is effected.

In one embodiment, the phrase "recovering the recombinant polypeptide or protein" used herein refers to collecting the whole fermentation medium containing the polypeptide or protein and need not imply additional steps of separation or purification.

In one embodiment, polypeptides or proteins of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the polypeptide or proteins of the present invention and fused cleavable moiety. In one embodiment, a fusion protein can be designed so that the polypeptide or protein can be readily isolated by affinity chromatography; e.g., by immobilization on a column specific for the cleavable moiety. In one embodiment, a cleavage site is engineered between the polypeptide or protein and the cleavable moiety and the polypeptide or protein can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the polypeptide or protein of the present invention is retrieved in "substantially pure" form.

In one embodiment, the phrase "substantially pure" refers to a purity that allows for the effective use of the protein in the applications described herein.

In one embodiment, the polypeptide or protein of the present invention can also be synthesized using in vitro expression systems. In one embodiment, in vitro synthesis methods are well known in the art and the components of the system are commercially available.

In another embodiment, the sulfated polysaccharides products produced by the methods as described herein are used in the cosmetic industry. In another embodiment, the sulfated polysaccharides products produced by the methods as described herein are used in cosmetic formulations.

In some embodiments, the proteins or oligonucleotides of the invention modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified proteins or oligonucleotides of the invention exhibit substantially longer half-lives in blood following intravenous injection than do the corresponding unmodified compounds. In one embodiment, modifications also increase the proteins or oligonucleotides solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

In one embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Experimental Procedures

Strains and Growth Conditions

Alga and Growth Conditions

*Porphyridium* sp. (UTEX 637) from the culture collection of the University of Texas was grown in 250-ml Erlenmeyer flasks, each containing 100 ml of culture, at 25±3° C. in artificial seawater (ASW) (Jones et al., 1963). Illumination was supplied continuously from above by fluorescent cool-white lamps at a photon flux density of 90 mmol photons $m^{-2}$ $s^{-1}$ for Erlenmeyer flasks. Cells were counted with a hemocytometer using a Zeiss light microscope.

Preparation of Desulfated Polysaccharide

Cultures in stationary growth (8-10 days) were centrifuged (9000×g 10 min) to separate the cells. The cells were washed once and resuspended to a final concentration of 15×10$^6$ cells ml$^{-1}$ in sulfate-free medium prepared by substituting the sulfate salts (MgSO$_4$.7H$_2$O) in the ASW with chloride salts (MgCl$_2$.6H$_2$O) (Frenkel, 1999). After four cycles of sulfate starvation, the supernatant containing the soluble desulfated polysaccharide was collected and dialyzed (2.3 cm diameter dialysis tubes, MW cut-off 8000) against distilled water at 4° C. until the conductivity of the water reached 1 µS. The final dialysate was autoclaved and used for further experiments. Sulfur content in the polysaccharide was reduced from 3.2% to 1.8%, as determined by the method of Terho and Hartiala (1978).

Isolation of mRNA and Construction of cDNA Libraries

Total RNA from *Porphyridium* sp. was isolated using TRI-REAGENT® (Molecular Research Center, Cincinnati, Ohio, USA) a reagent for the isolation of total RNA, according to the manufacturer's protocol. A high salt solution (0.8 M sodium citrate, 1.2 M NaCl) was added for purification from polysaccharide according to Chomczynski and Mackey (1995). Poly(A)$^+$ mRNA was isolated using oligo dT$_{25}$ magnetic DYNABEADS® (Dynal, Norway) magnetic beads, according to the manufacturer's instructions. The cDNA libraries were constructed with poly(A)$^+$ mRNA using the SMART cDNA Library construction kit (Clontech, Palo Alto, Calif., USA), after which cDNA was cloned into a plasmid pTriplex 2.

Expressed Sequence Tag Sequencing

Plasmids from 8,000 randomly picked bacterial clones were extracted and sequenced by Agawa, Germany. In addition, 2000 plasmids were sequenced at the Sequencing Service in the National Institute for Biotechnology in the Negev, located at Ben-Gurion University of the Negev (BGU). The sequencing data was stored in a database.

Total *Porphyridium* sp. DNA Extraction

Total genomic DNA was isolated by a modified CTAB protocol (Patwary and van der Meer, 1994). *Porphyridium* sp. cells were centrifuged (4000×g, 10 min) and resuspended twice with water acidified to pH 4 with HCl to wash cell surface-bound polysaccharide complexes, homogenized with CTAB buffer (3% CTAB, 1.4 M NaCl, 20 mM EDTA, 10 mM Tris, pH 8.0, 0.2% β-mercaptoethanol), and incubated at 65° C. for 2 h. The homogenate was then extracted with chloroform:isoamyl alcohol (24:1). DNA from the aqueous phase was precipitated with isopropanol, incubated with RNAse for 1 h, and then precipitated with ethanol and sodium acetate. The pellet was then washed with 70% alcohol and dissolved in Tris-EDTA buffer (TE). Nuclear and plastid DNA were separated on a CsCl-bisbenzimide density gradient (Boyen et al., 1994) by ultracentrifugation with a fixed angle Beckman Ti50 rotor at 40000 rpm for 40 h at 20° C. The bands were visualized under UV illumination and cut from the gel. DNA fractions were then dialyzed in TE buffer and extracted as described below.

Isolation of the ST Gene from *Porphyridium* sp.

The full-length sequence of the ST gene was amplified using the DNA walking Speed Up™ Kit according to the manufacturer's instructions (SeeGene, USA). The DNA walking primers were a combination of Annealing Control Primers (ACP) and specific primers designed based on the EST sequence of the ST gene. The PCR was run according to the manufacturer's instructions with annealing temperatures set for each of the primer combinations: first PCR-55° C. (primers combined: SulDWr1 5'-GCAATGTCGGGCG-GTCTG-3' (SEQ ID NO: 4) and DW-ACP 5'-ACP-A/C/G/T GGTC); second PCR-60° C. (primers combined: DW-ACP-N 5'-ACPN-GGTC and SulDWr2 5'-TCTGC-CTCGGTGACTTCGGC-3') (SEQ ID NO: 5); third PCR-63° C. (primers combined: Universal 5'-TCACAGAAG-TATGCCAAGCGA (SEQ ID NO: 6) and SulDWr3 5'-GCGTCGCCTATGTATTTCCGCCG-3') (SEQ ID NO: 7) using TAKARA LA TAQ® DNA polymerase (Takara, Kyoto, Japan), a combination of a Taq DNA Polymerase and a DNA proofreading polymerase with 3' to 5' exonuclease activity that is optimized for PCR amplification of very long DNA templates. The PCR products were sequenced by the sequencing service of BGU.

Southern Hybridization

Nuclear and organellar DNA—10 µg aliquots—were digested with EcoRI and fractionated on a 0.7% (w/v) agarose gel. The gel was treated with 0.25 N HCl, then denaturized (0.5 N NaOH, 1.5 N HCl) and neutralized (1 M Tris, 1.5N NaCl). The DNA was then transferred to a Nytran supercharged nylon membrane (Schleicher & Schuell Bioscience, Keene, N.H., USA) by capillary blotting. The blots were hybridized with random primed labeled [α$^{32}$P] ST and AHAS genes generated by PCR (ST: 926 bp fragment amplified with forward primer 5'-CACTTGCGTTGCCAC-CTTCATCC-3' (SEQ ID NO: 8) and reverse primer 5'-CTC-CGAAAGTCGCACAAGGC-3' (SEQ ID NO: 9); AHAS: 622 bp fragment amplified with forward primer 5'-CCAG-GTATTATTCTAGACTGAACT-3' (SEQ ID NO: 10) and reverse primer 5'-GAAATCCTGGTATTCTTGCTTCAC-3' (SEQ ID NO: 11)). Hybridization was carried out at 65° C. for 18 h, followed by a single wash in 2×SSC, 0.1% SDS at room temperature for 15 min. The blots were exposed to X-ray film overnight (Kodak BioMax MR film)

Cloning and Expression of the ST Gene from *Porphyridium* sp.

The bacterial expression constructs were prepared using forward (5'-CCCGAATTCATGTCGGGAGATGGGATGC) (SEQ ID NO: 12) and reverse (5'-CCC AAGCTTCGCCAATGCAAATCGGGCT) (SEQ ID NO: 13) oligonucleotide primers, the sequences of which were based on the beginning and the end of the coding regions of the ST sequence and on the DNA walking results described above. Restriction sites (underlined) to EcoRI and HindIII were added to the 5' ends of the primers. A PCR was run on a 100 μl reaction mixture using TAKARA LA TAQ® DNA polymerase (Takara, Kyoto, Japan), a combination of a Taq DNA Polymerase and a DNA proofreading polymerase with 3' to 5' exonuclease activity that is optimized for PCR amplification of very long DNA templates, with *Porphyridium* sp. DNA. Amplification conditions were 1 min at 94° C., 1 min at 55° C., and 1 min at 72° C. for 25 cycles. The reaction mixture was applied to a 1% agarose gel, separated by electrophoresis, and visualized by ethidium bromide staining. The detected PCR product was excised from the gel, and the DNA fragment therein was isolated by a gel extraction Kit (QIAQUICK® Gel Extraction, Qiagen, Hilden, Germany). Purified PCR product was restricted with EcoRI and HindIII restriction endonucleases, and subcloned into the EcoRI and HindIII site of the prokaryotic expression vector pET32a (Novagen, Darmstadt, Germany).

Three different constructs, each with the His-tag in a different position, were prepared in the pET32a vector and named according to His-tag location: a C-terminus construct (designated F+R), an N-terminus construct (designated F+R1), and a C&N-termini construct (designated F+R2) of *Porphyridium* sp. ST. The resulting constructs were amplified in *E. coli* DH5α cells and purified with a QIAGEN® plasmid mini prep kit (Qiagen, Hilden, Germany). The inserts were subjected to nucleotide sequencing using M-13 forward and reverse primers.

Bacterial Expression and Purification of the Recombinant *Porphyridium* sp. ST

The pET32a vectors harboring the cloned *Porphyridium* sp. ST were transformed into competent *E. coli* BL21(DE3) cells (Novagen, Darmstadt, Germany). Transformed BL21 (DE3) cells were grown to $\approx OD_{600\ nm}$ 0.5 in 1 ml LB medium supplemented with 100 μg/ml ampicillin and induced with 0.5 mM IPTG. After 3 h of induction at 37° C., the cells were harvested by centrifugation at 6000×g for 10 min at 4° C. and resuspended in a mixture of 5 ml ice-cold lysis buffer (50 mM $NaH_2PO_4$, 300 mM NaCl, 10 mM imidazole) 15 μl PMSF (protease inhibitor: 0.1 mM EGTA, 0.25% Tween 20, 2% Tritron X-100 pH 8.0), and frozen-thawed in liquid nitrogen. After sonication, the lysate was centrifuged at 10,000×g for 30 min at 4° C. The purification procedure for recombinant protein was carried out at 4° C., and 4 ml of soluble fraction containing recombinant protein were loaded on a 1-ml, 50% Ni-NTA column (6×His tag purification, Qiagen, Hilden, Germany). The bound His-tag fusion protein was washed twice with 4 ml wash buffer (50 mM $NaH_2PO_4$, 300 mM NaCl, 20 mM imidazole, pH 8.0) and then eluted by adding 0.5 ml of elution buffer (50 mM $NaH_2PO_4$, 300 mM NaCl, 250 mM imidazole, pH 8.0). The enzymatic activity of the purified recombinant sulfotransferase was analyzed.

Polyclonal Antiserum Preparation

Polyclonal antiserum against the His-tagged recombinant ST (F+R construct) protein was generated by injecting the purified fusion protein with complete Freund's adjuvant (CFA) into a rabbit four times with two-week intervals between injections.

Extraction of Cellular Proteins

*Porphyridium* sp. cells were washed twice with acidified water (pH 4) and resuspended at a concentration of $10^9$ cells $mL^{-1}$ in extraction buffer (Hepes 0.05M, pH 7). The cells were broken by four freeze-thaw cycles in liquid $N_2$. The homogenate was then centrifuged (10,000×g, 30 min), and a supernatant comprising soluble proteins was separated. The sediment was resuspended in homogenizing buffer (Hepes 0.05 M, pH 7, Triton x-100 1% (v/v)) and subjected to four freeze-thaw cycles in liquid $N_2$. The homogenate was then centrifuged (10,000×g, 30 min), and the supernatant containing the free membrane proteins was collected.

SDS-PAGE

Extracted protein samples (soluble and membrane bound) were analyzed by boiling each sample for 5 min in Laemmli buffer containing bromophenol blue in 0.125 M Tris-HCl, glycerol 20% (v/v), SDS 4% (w/v), and β-mercaptoethanol 10% and then analyzed by SDS-PAGE (Laemmli, 1970). The resolving gel was stained with Coomassie blue (Dunn, 1989).

Western Blot Analysis

Proteins were resolved by SDS-PAGE containing resolving gel (12% acrylamide) and stacking gel (5% acrylamide) and transferred to a nitrocellulose membrane according to Towbin et al. (1979). Blocked with 5% (w/v) low-fat dried milk, the membrane was then probed with the indicated antiserum (1:1000 dilution), followed by horseradish peroxidase (HRP) conjugated anti rabbit antibody. The membrane was incubated with a chemiluminescence (ECL) substrate (Amersham, Piscataway, N.J., USA), and antigen-antibody complexes were detected by exposure to X-ray film for 1-10 min (Kodak BioMax MR film).

Enzymatic Assay

The activity of O-sulfotransferase was determined according to Wlad et al. (1994) by measuring the incorporation of $^{35}SO_4$ from labeled PAPS into the O-desulfated polysaccharide of *Porphyridium* sp. In a total volume of 100 reaction mixtures contained 0.1 μCi of $[^{35}S]PAPS$, 1 mM unlabeled PAPS (purchased from Mercury), 15 μg substrate (O-desulfated polysaccharide of *Porphyridium* sp.), purified recombinant *Porphyridium* sp. ST enzyme, 50 mM Hepes (pH 7), 10 mM MnCl, 10 mM MgCl, 5 mM $CaCl_2$, 2 mM NaF, and 1 mM ATP. After incubation at 37° C., the reaction was terminated by the addition of 400 μl of ethanol. Polysaccharide was precipitated by centrifugation at 10,000×g for 30 min. The $^{35}S$-labeled polysaccharide was separated from residual labeled $[^{35}S]PAP$ by suspension of the polysaccharide pellet in 200 μl of water, re-precipitation by 80% ethanol, and six 10-min centrifugation cycles at 10,000×g for 10 min. To find the optimal reaction conditions, the assay was carried out at variable enzyme concentrations, time scales, and substrate concentrations of O-desulfated polysaccharide. All experiments were performed in triplicate.

Determination of Radioactivity

The extent of $[^{35}S]$ labelling in the polysaccharide was determined in vials containing 3 ml of ULTIMA GOLD XR (Packard BioScience B.V., The Netherlands) scintillation fluid and counted in a Beckman LS 1701 liquid scintillation counter.

Statistical Analysis

Statistical significance was determined by a Student's T test with P<0.05.

Example 1

Molecular-Cloning of the Novel Algal ST

A number of cDNA libraries of *Porphyridium* sp. were constructed, and EST databases were recently established with 2,062 non-redundant sequences (Lapidot et al., 2008). Screening of the non-redundant databases revealed a single open reading frame (ORF) of 730 bp, which was found to have 29% homology to mammalian origin dermatan-4-β- sulfotransferase (D4ST). Based on this information, the full-length sequence of the gene was amplified using Seegene's DNA Walking Speed Up™ Kit, as described in Materials and Methods. The 1155-bp ORF predicted a protein of 385 amino acid residues with a molecular mass of 43 kDa and two potential N-linked glycosylation sites (FIG. 1). A hydrophobic segment comprising 22 amino acid residues in the $NH_2$-terminal region was predicted using the Kyte-Doolittle hydrophobicity profile scale. Such a type II membrane-spanning domain is characteristic of many Golgi-localized STs and glycosyltransferases (Kitagawa et al., 2000).

Figure 2:
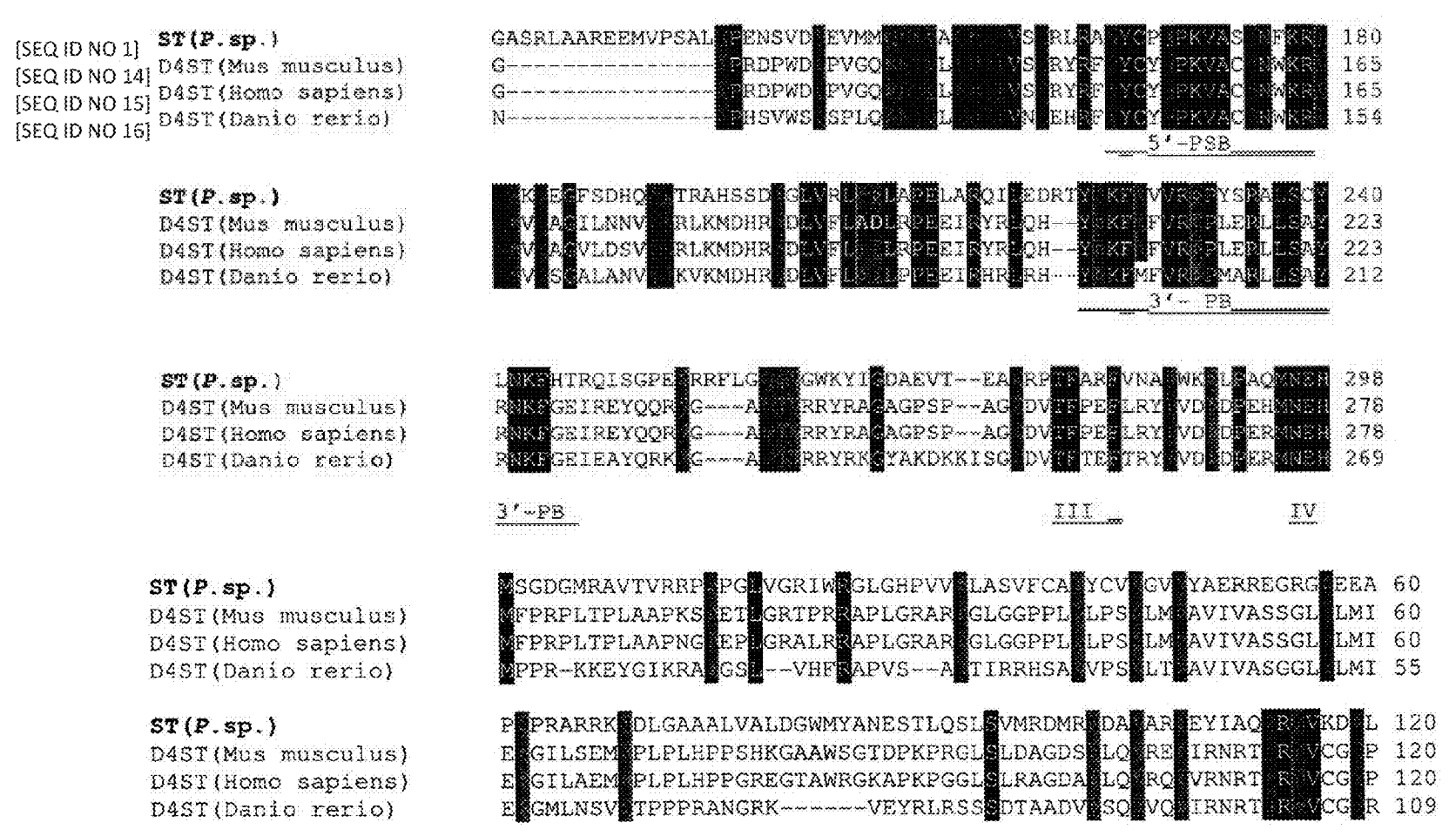

The clustalW algorithm was used to align multiple protein sequences of algal sulfotransferase with other D4STs of various species (FIG. 2). The regions showing the highest degree of homology are the putative 5'-PSB site, the putative 3'-PB binding site, and three regions of unknown function designated III, IV, and V at the carboxyl terminal (Hiraoka et al., 2000). The three regions of the carboxyl terminal may be substrate binding sites. Found in all STs cloned to date and based on X-ray crystallographic analysis of estrogen STs, the 5'-PSB and the 3'-PB binding sites were predicted to be consensus binding motifs to the high-energy PAPS donor (Sueyoshi et al., 1999).

Example 2

Identification of the ST Encoding Genome

To determine whether algal ST is encoded by the nuclear or organellar genome, total DNA was extracted from *Porphyridium* sp. cells and separated on a $CsCl_2$ gradient with an ultracentrifuge. The ST probe hybridized exclusively with nuclear DNA whereas an organellar probe derived from the AHAS gene of *Porphyridium* sp. proved to be encoded by the chloroplast genome (Lapidot et al., 1999) and hybridized only with organellar DNA (FIG. 3).

The amino acid alignment of the translated full sequence revealed 30% homology and 49% resemblance to mammalian D4ST. The sequence was found to have a single type II membrane domain. Southern blot analysis on organellar and nuclear fractions indicated that this algal ST is encoded by the nuclear genome, where it exists only as a single copy.

Amino acid alignment analysis of algal ST has revealed a conserved core structure for the PAPS binding sites: 5'-PBS and 3'-PB (Hiraoka et al., 2000; Kang et al., 2002; Yamauchi et al., 2000). Thirty one amino acid residues from $Leu^{156}$ to $Gly^{186}$ and 22 amino acid residues from $Tyr^{223}$ to $Phe^{244}$ correspond to the 5'-PSB and 3'-PB motifs, respectively. Ionic and hydrogen bonds between PAPS and $Arg^{230}/Arg^{235}$ or $Ser^{238}$ in the 3' PB domain are also thought to be crucial to this interaction. Based on this analysis of the algal ST, these amino acids are fully conserved in its sequence. Another residue essential in the 5'-PSB motif is $Arg^{163}$. Although some substitutions are evident in the corresponding residues of the algal ST, the amino acid similarities at these positions are conserved. The regions with the lowest percentage of identical amino acids include the transmembrane domain in the N-terminal region and possible substrate-binding sites in the C-terminal regions of the algal ST sequence.

Example 3

Cellular Localization of the ST

Figure 4:
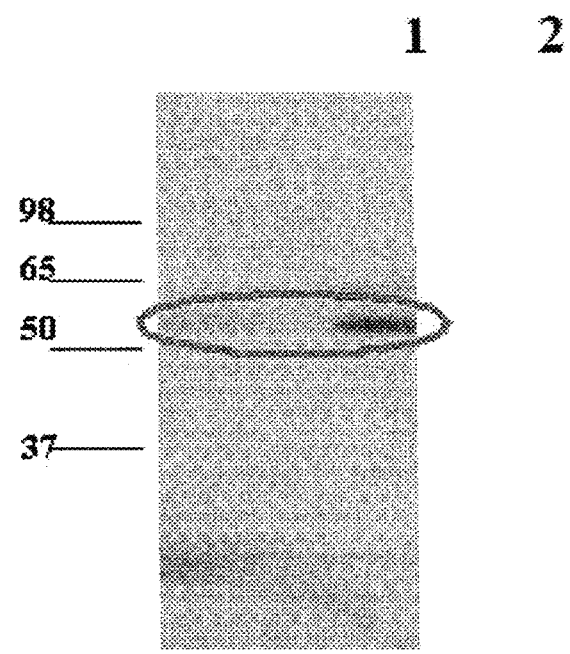
FIG. 4: Is a micrograph showing western blot analysis of proteins from *Porphyridium* sp. probed with anti-ST antiserum. Lane 1—total protein extracted from the soluble fraction. Lane 2—total protein extracted from the membrane fraction. Each lane was loaded with 10 μg of protein extracts. Molecular weight markers (kDa) are shown to the left of lane 1.

The ST family comprises the major classes of cytosolic and membrane-associated STs, the location of which inside the algal cell was characterized by western blot analysis. Extracts of soluble and membrane-bound protein were separated on SDS-PAGE, transferred to a nylon membrane, and probed with anti ST antibodies (FIG. 4). Western blot analysis indicated that most of the ST is located in the membrane-bound fraction, from which it can be inferred that the ST is a membrane-associated ST that sulfonates large polysaccharide molecules.

Example 4

Expression and Purification of Bacterially Expressed *Porphyridium* Sp. ST

The full-length cDNA of ST from *Porphyridium* sp. was amplified with primers containing restriction sites of the endonucleases EcoRI and HindIII at its 3' and 5' ends, respectively; cloned into a pET32a vector; and digested with the same restriction endonucleases. Soluble ST of *Porphyridium* sp. was then expressed at high levels in *Escherichia coli* (*E. coli*) BL21(DE3) cells from the pET32a vector, upon induction with 0.5 mM isopropyl-D-1-thiogalactopyranoside (IPTG).

Figure 5A:
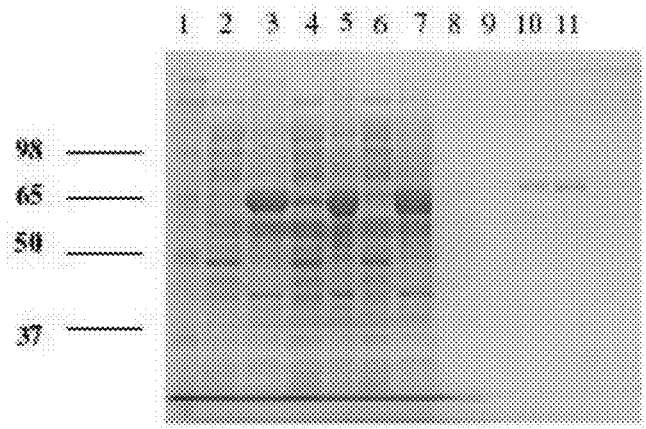
FIG. 5. Shows micrographs of SDS-polyacrylamide gel electrophoresis (A) and western blot analysis (B) of native algal ST expressed and purified from *E. coli* BL21 (DE3). (A) Lane 1—protein size markers. Lanes 2, 4, 6—soluble protein fraction of transformed *E. coli* cells, after 3 h induction with 0.5 mM IPTG, of constructs F+R, F+R1, and F+R2, respectively. Lanes 3, 5, 7—non-soluble protein fraction of transformed *E. coli* cells, after 3 h induction with 0.5 mM IPTG, of constructs F+R, F+R1, and F+R2, respectively. Lanes 8-11—fractions of purified native algal ST protein from transformed *E. coli* cells from the F+R construct, using a Ni-NTA column. (B) Lanes 1, 2, 3—purified ST enzyme from recombinant *E. coli* cells of constructs F+R, F+R1, F+R2, respectively. Lane 4—negative control (proteins extracted from non-transformed *E. coli* cells). Molecular masses (kDa) are shown to the left of lane 1. Proteins were detected using rabbit antibodies against the recombinant ST (F+R).
Figure 5B:
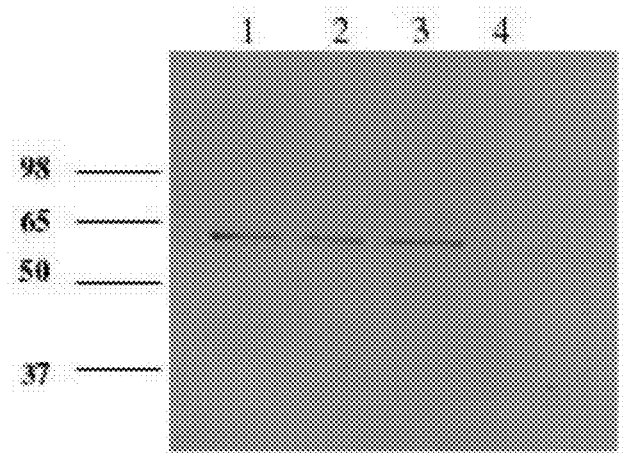

To ensure that the $(His)_6$ tag (His-tag) would not affect enzyme activity after purification, three different constructs were used, thereby locating the His-tag in different positions: C-terminus construct (rephrased F+R construct), N-terminus construct (rephrased F+R1 construct), and C&N-terminus (rephrased F+R2 construct) of the ST of *Porphyridium* sp., as described in Materials & Methods. Thus, three *Porphyridium* sp. ST constructs each with a predicted molecular mass of 64.5 kDa (43 kDa predicted from the cDNA of ST, which contained 385 amino acids, with the residual mass comprising the His-tag and the 173 amino acid gap between the tag and the cloning site of the ST) were used throughout this study. All constructs were successfully expressed in *E. coli* BL21(DE3) cells as shown by SDS-PAGE (FIG. 5A). The expressed constructs were collected by centrifugation, freezing/thawing, sonication, and then centrifugation again. The resulting supernatant was purified from the total bacterial proteins by using Ni-NTA column chromatography and under native conditions. As expected, the molecular weight of the purified *Porphyridium* sp. ST was approximately 64.5 kDa, as shown on SDS-PAGE (FIG. 5). With antibodies prepared against the recombinant *Porphyridium* sp. ST, it was shown that the purified enzyme was the recombinant *Porphyridium* sp. ST (FIG. 5B).

The algal ST was successfully expressed in H is fusion form, and optimal conditions for its expression were set. To maintain the enzyme in its active form, soluble, recombinant algal ST was purified under native conditions. STs from the three plasmids used (F+R, F+R1, F+R2) were obtained in their native forms.

Example 5

Enzymatic Characterization of *Porphyridium* Sp. ST

Optimal conditions—pH, temperature, enzyme concentration, reaction time, and substrate concentration—were characterized to determine the activity of *Porphyridium* sp. ST. Recombinant *Porphyridium* sp. ST protein activity was then measured using the O-desulfated *Porphyridium* sp. polysaccharide as the acceptor of the $^{35}SO_4$ groups transferred from $PAP^{35}S$ and as the substrate for the reaction.

Figure 6:
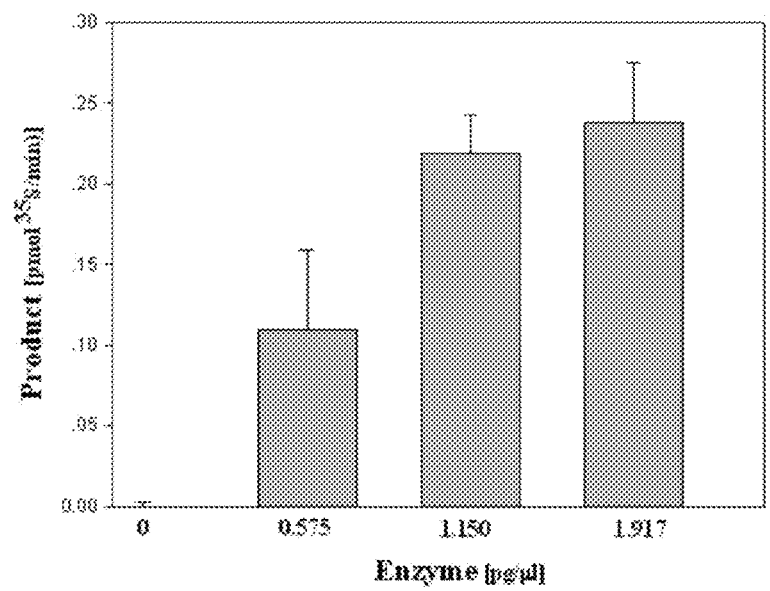
FIG. 6. Is a bar graph showing the effect of ST concentration on the sulfation of O-desulfated algal polysaccharide. Each reaction contained 0.015 mg/ml of O-desulfated polysaccharide, 10 μM [35S] PAPS, and progressively increasing concentrations of the F+R recombinant enzyme, as shown on the graph. Each point is an average of triplicate reactions.
Figure 7:
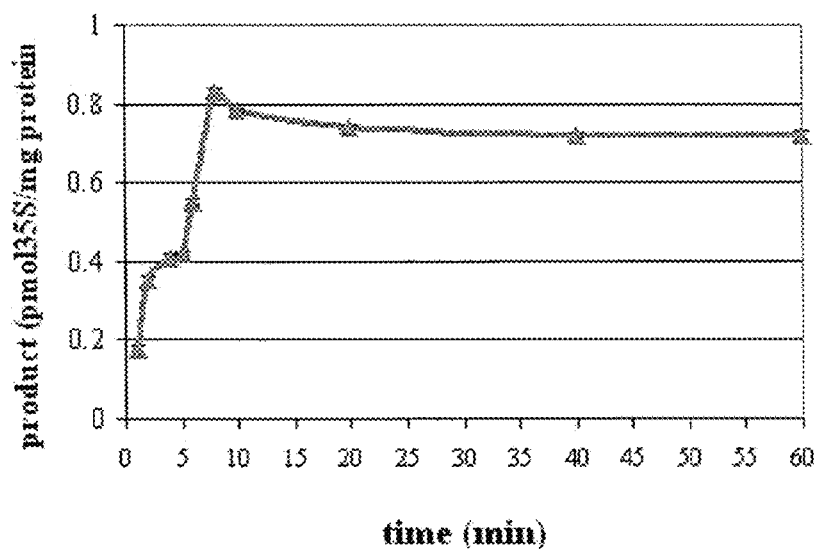
FIG. 7. Is a graph showing the activity of recombinant algal ST as a function of time. Each reaction contained 0.015 μg/μl O-desulfated polysaccharide, 1.917 pg/μl recombinant F+R enzyme, and 10 μM [35S] PAPS. The mixtures were incubated at 37° C. Each point is an average of triplicate reactions.
Figure 8:
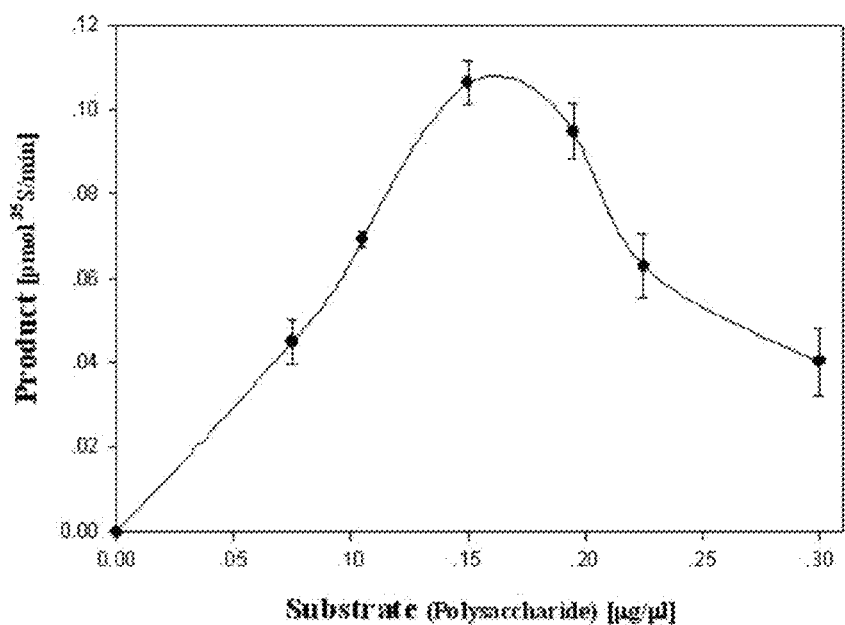
FIG. 8. Is a graph showing the effect of substrate concentration (O-desulfated polysaccharide) on recombinant ST activity. Subsequent assays involved progressively increasing concentrations of the substrate. Each reaction contained 1.917 pg/μl F+R enzyme and 10 μM [35S] PAPS, and the mixtures were incubated for 10 min at 37° C. Each point is an average of triplicate reactions.

Preliminary assay reactions indicated that optimal activity was obtained at pH 7 and 37° C. (data not shown). Different recombinant *Porphyridium* sp. ST concentrations (0-1.917 pg/μl), were used, which revealed that sulfation increased with enzyme concentration (FIG. 6). In the calculation of ST activity, the radioactivity of 35 S bound to the polysaccharide in the absence of enzyme was subtracted. Optimal incubation time of the sulfation reaction was determined (FIG. 7). The results show that sulfation activity was proportional to time during the first 8 min, after which concentration of the product did not increase (see Discussion). Optimal reaction time, therefore, was set to 8 min and used in subsequent experiments. In testing for the effect of substrate concentration on ST activity, maximum sulfation activity was obtained at a concentration of 0.015 μg/μl of desulfated polysaccharide (FIG. 8).

The substrate used in this work was the algal polysaccharide purified from the cells grown under sulfate starvation, which resulted in a subsequent decrease in its sulfate content. The algal ST appeared to act on the algal polysaccharide at different enzyme concentrations, but it was sensitive to the changes in the polysaccharide concentration.

Based on these analyses, assay conditions for the *Porphyridium* sp. ST were set as follows: 1.917 μg/μl recombinant ST, incubation time 8 min, and a substrate concentration of 0.015 μg/μl O-desulfated algal polysaccharide. Under these conditions, all three ST constructs (F+R, F+R1, F+R2) showed significant ST activity, and between the constructs there were only negligible differences: 0.123±0.005 [pmol $^{35}$S/min*mg protein], 0.118±0.016 [pmol $^{35}$S/min*mg protein], and 0.11±0.003 [pmol $^{35}$S/min*mg protein] for F+R, F+R1, and F+R2, respectively.

These results indicate that the recombinant *Porphyridium* sp. ST can sulfonate the algal polysaccharide regardless of the location of the His-tag. However, yet to be determined whether the tags affect the kinetic properties of the recombinant protein.

The recombinant algal ST displayed pH and temperature dependence. *Porphyridium* sp. is normally maintained in Erlenmeyer flasks heated to 25±3° C. (Jones et al., 1963). In their natural habitat, however, they are subjected to temperature fluctuations caused by tidal changes. An intriguing issue, therefore, is the stability of the enzyme at different temperatures, when the optimal temperature for activity is 37° C.

The enzyme showed optimum activity after an incubation time of 8 min, the extension of which produced no change in product formation.

All plasmids (F+R, F+R1, F+R2) used in this experiment reacted similarly with the algal polysaccharide, thus indicating that the ST enzyme was not affected by the location of the His-tag and that it was produced from the bacterial cells in their active form.

Thus, the present examples show for the first time the existence of novel ST in algal cells. This finding can be applied to help us manipulate the sulfation process and produce new, enzymatically sulfated polysaccharides with elevated sulfate contents.

Example 6

Over Expression of the Sulfotransferase in *Porphyridium* Sp. Cells

For this purpose the sulfotransferase gene was cloned into a eukaryotic expression vector under the control of the heterologous promoter CaMV35S. CaMV35S is a strong constitutive promoter and its widely used for expression of genes in plants and plant tissue cultures. CaMV35SpolyA termination sequence was added downstream to the sulfotransferase gene. Sh ble gene was also cloned to this vector flanked by CaMV35S promoter and CaMV35SpolyA termination sequences. Sh ble gene was used as a selectable marker for zeocin resistance. Previous experiments showed that the cells of *Porphyridium* sp. are sensitive to small concentrations of zeocin.

Preparation of pSTshort-shble and pSTlong-sh ble Vectors for Over Expression.

Figures 9A, 9B:
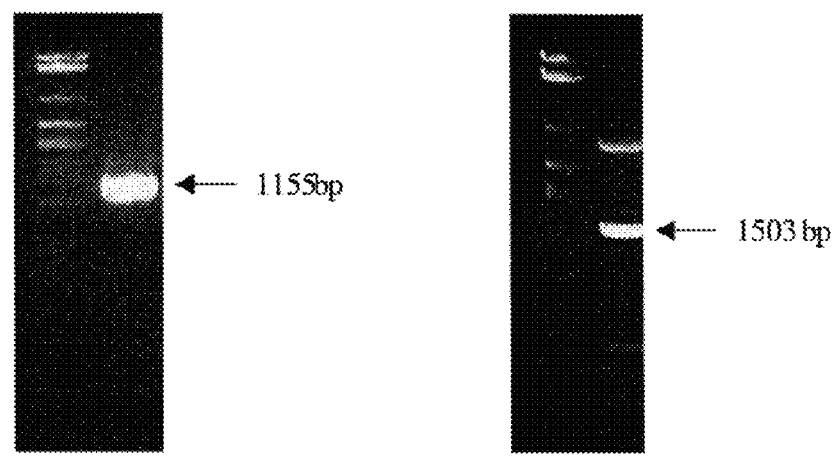
FIG. 9. Depicts a gel micrograph showing: (A) in the right lane the short sequence (ST-short) containing 1155 bases, a size marker is provided in the left lane; and (B) in the right lane the long sequence (ST-long) containing 1503 bases, a size marker is provided in the left lane.

The inserts: two ORFs of sulfotransferase gene from *Porphyridium* sp. were amplified from total DNA by PCR. The long ORF (STlong) which contains 1503 bp and short ORF (STshort) which contains 1155 bp. Recognition sites of restriction enzymes HindIII and SpeI were added to the 5' end of the forward and reverse primer respectively. The DNA bands were extracted from the gel followed by restriction with HindIII and SpeI (see FIG. 9).

Figure 10:
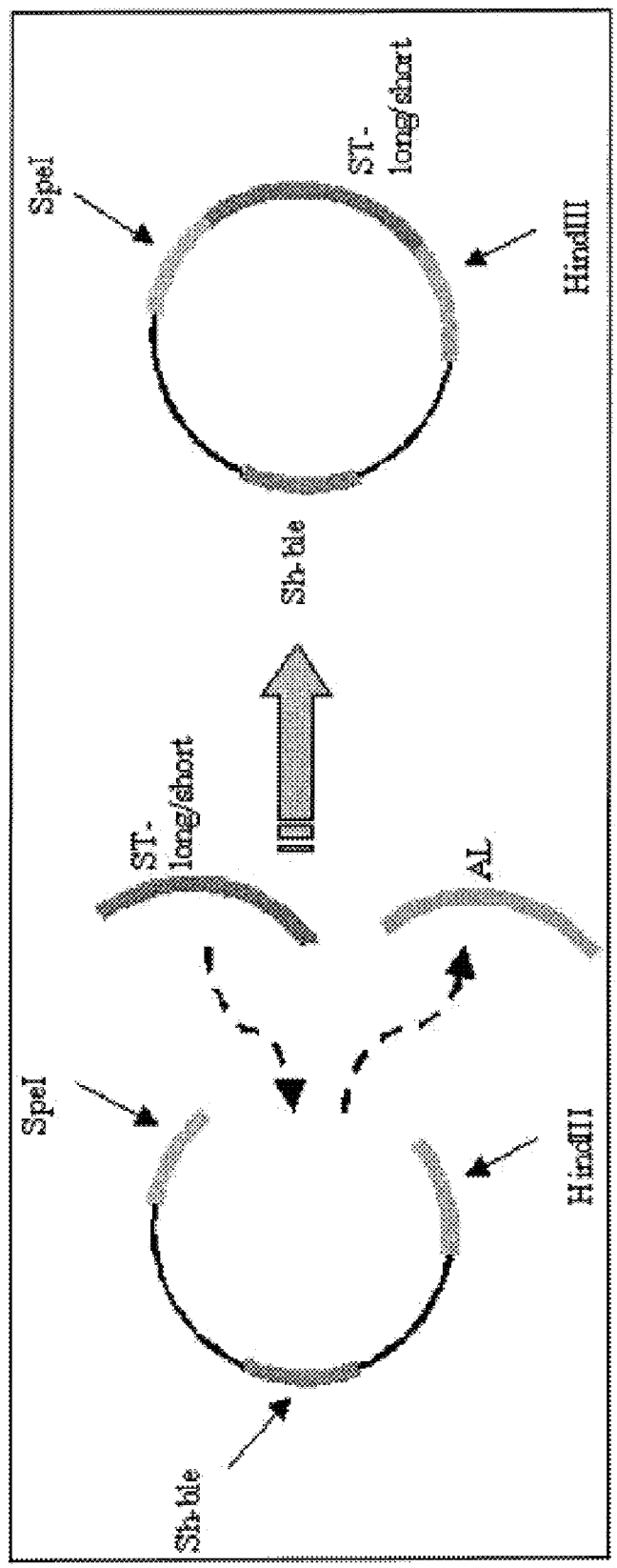
FIG. 10. Is an illustration of the plasmid, the inserts and the restriction enzymes utilized in example 6. The vector pAL-sh ble was cut with the same restriction enzymes as the insert in order to pull out the AL gene followed by one ligation with the ST-long insert and one ligation with the ST-short insert.

Ligation of the inserts into the vectors: the vector pAL-sh ble was cut with same restriction enzymes as insert to pull out the AL gene and ligated once with STlong and once with STshort insert (FIG. 10). After the ligation plasmids were transformed to *E. coli*. *E. coli* cultures containing pSTlong-sh ble and pSTlong-sh ble were grown overnight and the plasmids were extracted and subjected to restriction with HindIII and SpeI to verify inserts presence (results not shown).

Transformation to Red Microalga *Porphyridium* Sp.

The plasmids pSTlong-sh ble and pSTlong-sh ble were transformed to algal cells for over-expression of the sulfotransferase. For this purpose cells and plasmid were agitated for 25 seconds in the presence of very small glass beads (0.5 mm). After transformation, the cells were transferred to beakers containing ASW medium and 6 μg/ml zeocin, for selection of the transformants. Cell were grown for 14 days. Additionally, the transformed cell were spread onto Petri dishes with ASW+1.5% agar and 4 μg/ml zeocin. Colonies appeared after 3 weeks.

PCR Characterization of the Transformants.

Figure 11:
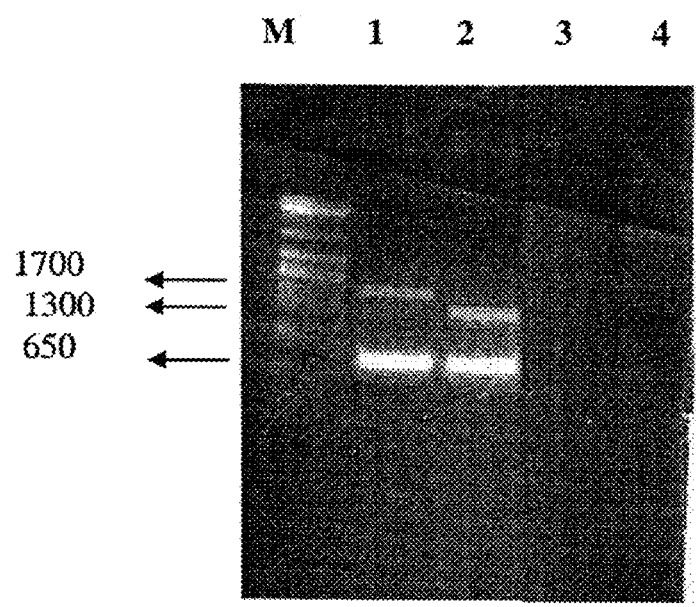
FIG. 11. Depicts a gel micrograph. Lane M is the size marker, lane 1 is the DNA extracted from alga (TR-2) after transformation with the plasmid pSTlong-ble, lane 2 is the DNA extracted from alga (TR-1) after transformation with the plasmid pSTshort-ble, lane 3 is the DNA extracted from wild-type alga, lane 4 is a negative control without DNA.

After transformation, the cells that survived in the selective media were collected by centrifugation for genomic DNA extraction. PCR reaction was performed with primers located in the end of CaMV35S promoter sequence and at the beginning of CaMV35S polyA sequence. In this case two products were expected, the first is the Sh ble gene (650 bp) and the second belongs to the ST-long (1700 bp). In cells transformed with pSTshort-sh ble two bands were expected, the first is the Sh ble gene 650 bp and the second is the ST-short (1300 bp). These expected products result from the fact that both Sh ble and ST were flanked by the same promoter and terminator sequence. Genomic DNA from wild type culture was used as control. The results in FIG. 11 confirm the expected products.

Characterization by Southern Blot

Southern blot analyses were used to test the presence of Sh ble sequences in DNA isolated from transformants TR-1 (transformed with pSTshort-sh ble) and from TR-2 (transformed with pSTlong-sh ble). Total DNA from wild type cells and transformants was digested with HindIII and probed with radioactive labeled 0.6 kb fragment containing the entire Sh ble coding region. HindIII cuts in a single site within the plasmid but in the Sh ble gene. Digestion of TR-1 and TR-2 with HindIII produces one fragment ~7000 bp which contain Sh ble gene in it. The Sh ble probe did not hybridize to DNA from wild type cells.

In order to test whether both copies of ST (native and transformed) are present in the transformants, DNA was digested with PstI enzyme that cuts at a single site at ST gene. Both copies were present in the genome of the transformants as viewed by probing with 1.5 kb fragment of ST gene-4 bands of varying sizes appeared. The DNA of wild type yielded as expected only two bands of 5500 and 4000 bp. Two additional bands of 10000 and 2500 in the TR-2 transformants were also detected. Thus both copies of ST are present in the transformants as expected.

Sulfur Content in the Polysaccharide of Transformants

Soluble polysaccharides from transformants and from wild type algal cultures were collected by centrifugation and subjected to sulfur content examination. As shown in Table 1 the sulfur content of the polysaccharide extracted from the transformant TR unexpectedly higher by 38% compared to the wild type cells. Thus over-expression of sulfotransferase results in greater sulfation.

TABLE 1 percent of sulfur in polysaccharides obtained from over-expressing sulfotransferase transformants and wild-type of *Porphyridium* SP.

| | Culture | |
|---|---|---|
| Content | W.T. | TR |
| Sulfur (% dry weight) | 3.5 ± 0.14 | 4.85 ± 0.09 |

The results show depict the absolute percentage of sulfur in polysaccharides (n=3). The polysaccharides were purified through dialysis and dried in a lyophilizer. The sulfur content was measured utilizing the potentiometric method of Hartiala and Terho.

---

What is claimed is:

1. A polynucleotide comprising a nucleic acid sequence operably linked to a heterologous promoter, wherein said nucleic acid sequence encodes the amino acid sequence set forth in SEQ ID NO: 1, wherein said nucleic acid sequence encoding the amino acid sequence set forth in SEQ ID NO: 1 is selected from SEQ ID NO: 2 or SEQ ID NO: 3.

2. A composition comprising a polynucleotide comprising a nucleic acid sequence operably linked to a heterologous promoter, wherein said nucleic acid sequence encodes the amino acid sequence set forth in SEQ ID NO: 1, wherein said nucleic acid sequence encoding the amino acid sequence set forth in SEQ ID NO: 1 is selected from SEQ ID NO: 2 or SEQ ID NO: 3.

3. An expression vector comprising a polynucleotide comprising a nucleic acid sequence operably linked to a heterologous promoter, wherein said nucleic acid sequence encodes the amino acid sequence set forth in SEQ ID NO: 1, wherein said nucleic acid sequence encoding the amino acid sequence set forth in SEQ ID NO: 1 is selected from SEQ ID NO: 2 or SEQ ID NO: 3.

4. A cell comprising an expression vector comprising a polynucleotide comprising a nucleic acid sequence operably linked to a heterologous promoter, wherein said nucleic acid sequence encodes the amino acid sequence set forth in SEQ ID NO: 1, wherein said nucleic acid sequence encoding the amino acid sequence set forth in SEQ ID NO: 1 is selected from SEQ ID NO: 2 or SEQ ID NO: 3.

5. A transgenic organism or a transformed bacteria transformed by a polynucleotide comprising a coding portion encoding the amino acid sequence set forth in SEQ ID NO: 1, wherein the nucleic acid sequence encoding the amino acid sequence set forth in SEQ ID NO: 1 is selected from SEQ ID NO: 2 or SEQ ID NO: 3.

6. The transgenic organism of claim 5, wherein said organism is a plant, a seed, or an alga.

7. A transgenic seed, produced by a transgenic plant transformed by a polynucleotide of claim 1.

8. A method of producing a sulfated polysaccharide in a cell comprising the step of transforming a cell with a polynucleotide of claim 1, thereby producing a sulfated polysaccharide in a cell.

9. The method of claim 8, wherein said cell is a plant cell or an algal cell.

10. A method of increasing the number of sulfur groups in a polysaccharide in a cell, comprising the step of overexpressing a polynucleotide sequence encoding a sulfotransferase in said cell, wherein said polynucleotide comprises a nucleic acid sequence that encodes a protein comprising the amino acid sequence as set forth in SEQ ID NO: 1, wherein said nucleic acid sequence is set forth in SEQ ID NO: 2 or SEQ ID NO: 3, thereby increasing the number of sulfur groups in a polysaccharide in a cell.

11. The method of claim 10, wherein said cell is a red microalga cell or a prokaryotic cell.

* * * * *

SEQUENCE LISTING

<160> NUMBER OF SEQ ID NOS: 16

<210> SEQ ID NO 1
<211> LENGTH: 384
<212> TYPE: PRT
<213> ORGANISM: Porphyra spiralis

<400> SEQUENCE: 1

```
Met Ser Gly Asp Gly Met Arg Ala Val Thr Val Arg Arg Pro Ala Pro
1               5                   10                  15

Gly Leu Val Gly Arg Ile Trp Arg Gly Leu Gly His Pro Val Val Ser
            20                  25                  30

Leu Ala Ser Val Phe Cys Ala Leu Tyr Cys Val Val Gly Val Tyr Tyr
        35                  40                  45

Ala Glu Arg Arg Glu Gly Arg Gly Phe Glu Glu Ala Pro Gln Pro Arg
    50                  55                  60

Ala Arg Arg Lys Asn Asp Leu Gly Ala Ala Ala Leu Val Ala Leu Asp
65                  70                  75                  80

Gly Trp Met Tyr Ala Asn Glu Ser Thr Leu Gln Ser Leu Ser Val Met
                85                  90                  95

Arg Asp Met Arg Asn Asp Ala Val Ala Arg Asp Glu Tyr Ile Ala Gln
            100                 105                 110

Leu Arg Ala Val Lys Asp Glu Leu Gly Ala Ser Arg Leu Ala Ala Arg
        115                 120                 125

Glu Glu Met Val Pro Ser Ala Leu Ile Pro Glu Asn Ser Val Asp Val
    130                 135                 140

Glu Val Met Met Gln His Ser Phe Ala Lys Arg Leu Ile Val Ser Gln
145                 150                 155                 160

Arg Leu Arg Ala Val Tyr Cys Pro Ile Pro Lys Val Ala Ser Thr Asn
                165                 170                 175

Phe Lys Arg Leu Ile Arg Lys Phe Glu Gly Phe Ser Asp His Gln Asn
            180                 185                 190

Leu Thr Arg Ala His Ser Ser Asp Ser Gly Leu Val Arg Leu Ser Glu
        195                 200                 205

Leu Ala Pro Glu Leu Ala Arg Gln Ile Leu Glu Asp Arg Thr Tyr Leu
    210                 215                 220

Lys Phe Val Val Arg Glu Pro Tyr Ser Arg Ala Leu Ser Cys Tyr
225                 230                 235                 240

Leu Asn Lys Phe His Thr Arg Gln Ile Ser Gly Pro Glu Phe Arg Arg
```

```
                245                 250                 255
Phe Leu Gly Gln Leu Val Gly Trp Lys Tyr Ile Gly Asp Ala Glu Val
            260                 265                 270

Thr Glu Ala Asp Arg Pro Thr Phe Ala Arg Phe Val Asn Ala Ile Trp
        275                 280                 285

Lys Gln Leu Pro Ala Gln Met Asn Glu His Trp Ala Ile Gln Ser Val
        290                 295                 300

Leu Cys Gly Ile Gly Val Ile Pro Tyr Asp Phe Val Gly Arg Phe Glu
305                 310                 315                 320

Glu Leu Pro Glu His Ala Leu Leu Ile Leu Arg Ala Leu Gly Lys Ser
                325                 330                 335

Ala Glu Ser Phe Pro Ser Pro Ser Glu Ile Gly Phe Leu Ser Thr Glu
            340                 345                 350

Ala Asn Thr Gln Leu Asp Ala Phe Tyr Thr Pro Ala Leu Arg Ser Ser
        355                 360                 365

Val Arg Glu Ile Tyr His Ala Asp Phe Asn Leu Leu Glu Tyr Ala Ile
    370                 375                 380

<210> SEQ ID NO 2
<211> LENGTH: 1155
<212> TYPE: DNA
<213> ORGANISM: Porphyra spiralis

<400> SEQUENCE: 2
atgtcgggag atgggatgcg agcggtgacg gttcgccgac ccgcgccggg cttggttggg      60
cgaatctggc gcgggctagg gcacccagtc gtgtcgcttg cgagcgtgtt ctgcgcgttg     120
tattgtgtcg tgggcgtgta ctatgccgag cgcagggaag ggcgcggctt cgaagaagcg     180
ccgcagccgc gtgcgcggcg gaaaaatgat ctgggcgcag cagccctagt ggctctggac     240
ggctggatgt acgcaaatga gtcgacgctg cagtcactgt cggtaatgcg tgacatgcgg     300
aacgacgctg tggcgagaga tgaatatatc gcgcaattgc gcgcagtcaa agacgagctc     360
ggtgcttcgc gcttagccgc cagagaggaa atggcccgt ctgctttgat tccggagaat     420
agcgtggatg tggaggtcat gatgcagcac tcctttgcca acggctcat tgtttcgcaa     480 cgcctgcgcg ccgtctactg tccgataccg aaagtggcta gcacaaattt caaacgcctg     540
atacgcaagt ttgaagggtt tagcgatcac cagaacctta cacgtgcaca ctcgagcgac     600
tctggccttg tgcgactttc ggagctcgcg ccggaattgg ctcggcaaat actcgaggac     660
cgcacgtacc tcaaattcgt ggtcgtgcgc gagccctact cgcgcgccct cagctgctac     720
ttgaacaagt tccacacgcg acaaattagc ggccctgagt tcggcgcttt ccttggccag     780
ctggtcggct ggaaatacat aggcgacgcc gaagtcaccg aggcagaccg cccgacattt     840
gcgcggtttg tgaacgccat ttggaagcaa ctacccgcgc agatgaacga gcactgggcg     900
atccagagcg ttttgtgcgg gataggcgtg atcccgtatg actttgtggg gcgcttcgag     960
gagctgcctg agcatgcgct gctcatcctg cgcgctctgg gaaagagtgc cgagtcgttt    1020
ccgagtccat ctgaaattgg attcctcagc accgaggcca acacgcagct cgatgcgttc    1080
tacacgccgg ctctacgcag cagcgtgcgc gaaatctacc acgcggactt taatttactc    1140
gagtacgcaa tctag                                                    1155

<210> SEQ ID NO 3
<211> LENGTH: 1503
<212> TYPE: DNA
<213> ORGANISM: Porphyra spiralis
```

<400> SEQUENCE: 3

```
atgacttgat cgcgcatccc gccctgctcg atcccagaat cgctgtcact tgcgttgcca      60
ccttcatcct gcaccatttt caccacgttg gccatcctgc ttcgacgcca catagccacc     120
cccacgcgcg cactcgctcc gcgcgacacg cgcgcgtccg cgatcacctt ggatccagcg     180
aacacgcttc ccgcccctac aaaacccatc gcaggtgcca tcttttttcac tcctcgaagc    240
cactttttgcc ctccaaagca cactcacaca cgtcgcgact caccacgact cgacgcacgc    300
ttgtcctccc cggctcatcc cggcagctgc cgcaatctcg ccgacaaaat gtcgggagat     360
gggatgcgag cggtgacggt tcgccgaccc gcgccgggct tggttgggcg aatctggcgc     420
gggctagggc acccagtcgt gtcgcttgcg agcgtgttct gcgcgttgta ttgtgtcgtg     480
ggcgtgtact atgccgagcg cagggaaggg cgcggcttcg aagaagcgcc gcagccgcgt     540
gcgcggcgga aaaatgatct gggcgcagca gccctagtgg ctctggacgg ctggatgtac     600
gcaaatgagt cgacgctgca gtcactgtcg gtaatgcgtg acatgcggaa cgacgctgtg     660
gcgagagatg aatatatcgc gcaattgcgc gcagtcaaag acgagctcgg tgcttcgcgc     720
ttagccgcca gagaggaaat ggtcccgtct gctttgattc cggagaatag cgtggatgtg     780
gaggtcatga tgcagcactc ctttgccaaa cggctcattg tttcgcaacg cctgcgcgcc     840
gtctactgtc cgataccgaa agtggctagc acaaatttca aacgcctgat acgcaagttt     900
gaagggttta gcgatcacca gaaccttaca cgtgcacact cgagcgactc tggccttgtg     960
cgactttcgg agctcgcgcc ggaattggct cggcaaatac tcgaggaccg cacgtacctc    1020
aaattcgtgg tcgtgcgcga gccctactcg cgcgccctca gctgctactt gaacaagttc    1080
cacacgcgac aaattagcgg ccctgagttt cggcgcttcc ttggccagct ggtcggctgg    1140
aaatacatag gcgacgccga agtcaccgag gcagaccgcc cgacatttgc gcggtttgtg    1200
aacgccattt ggaagcaact acccgcgcag atgaacgagc actgggcgat ccagagcgtt    1260
ttgtgcggga taggcgtgat cccgtatgac tttgtggggc gcttcgagga gctgcctgag    1320
catgcgctgc tcatcctgcg cgctctggga aagagtgccg agtcgtttcc gagtccatct    1380
gaaattggat tcctcagcac cgaggccaac acgcagctcc atgcgttcta cacgccggct    1440
ctacgcagca gcgtgcgcga aatctaccac gcggacttta atttactcga gtacgcaatc    1500
tag                                                                  1503
```

<210> SEQ ID NO 4
<211> LENGTH: 18
<212> TYPE: DNA
<213> ORGANISM: Artificial Sequence
<220> FEATURE:
<223> OTHER INFORMATION: Primer SulDWr1

<400> SEQUENCE: 4

```
gcaatgtcgg gcggtctg                                                    18
```

<210> SEQ ID NO 5
<211> LENGTH: 20
<212> TYPE: DNA
<213> ORGANISM: Artificial Sequence
<220> FEATURE:
<223> OTHER INFORMATION: Primer SulDWr2

<400> SEQUENCE: 5

```
tctgcctcgg tgacttcggc                                                  20
```

<210> SEQ ID NO 6
<211> LENGTH: 21
<212> TYPE: DNA
<213> ORGANISM: Artificial Sequence
<220> FEATURE:
<223> OTHER INFORMATION: Primer - Universal

<400> SEQUENCE: 6
tcacagaagt atgccaagcg a                                            21

<210> SEQ ID NO 7
<211> LENGTH: 23
<212> TYPE: DNA
<213> ORGANISM: Artificial Sequence
<220> FEATURE:
<223> OTHER INFORMATION: Primer SulDWr3

<400> SEQUENCE: 7
gcgtcgccta tgtatttccg ccg                                          23

<210> SEQ ID NO 8
<211> LENGTH: 23
<212> TYPE: DNA
<213> ORGANISM: Artificial Sequence
<220> FEATURE:
<223> OTHER INFORMATION: STforward primer

<400> SEQUENCE: 8
cacttgcgtt gccaccttca tcc                                          23

<210> SEQ ID NO 9
<211> LENGTH: 20
<212> TYPE: DNA
<213> ORGANISM: Artificial Sequence
<220> FEATURE:
<223> OTHER INFORMATION: STreverse primer

<400> SEQUENCE: 9
ctccgaaagt cgcacaaggc                                              20

<210> SEQ ID NO 10
<211> LENGTH: 24
<212> TYPE: DNA
<213> ORGANISM: Artificial Sequence
<220> FEATURE:
<223> OTHER INFORMATION: AHAS forward primer

<400> SEQUENCE: 10
ccaggtatta ttctagactg aact                                         24

<210> SEQ ID NO 11
<211> LENGTH: 24
<212> TYPE: DNA
<213> ORGANISM: Artificial Sequence
<220> FEATURE:
<223> OTHER INFORMATION: AHAS reverse primer

<400> SEQUENCE: 11
gaaatcctgg tattcttgct tcac                                         24

<210> SEQ ID NO 12
<211> LENGTH: 28
<212> TYPE: DNA
<213> ORGANISM: Artificial Sequence
<220> FEATURE:
<223> OTHER INFORMATION: forward primer

```
<400> SEQUENCE: 12
cccgaattca tgtcgggaga tgggatgc                                            28

<210> SEQ ID NO 13
<211> LENGTH: 28
<212> TYPE: DNA
<213> ORGANISM: Artificial Sequence
<220> FEATURE:
<223> OTHER INFORMATION: reverse primer

<400> SEQUENCE: 13
cccaagcttc gccaatgcaa atcgggct                                            28

<210> SEQ ID NO 14
<211> LENGTH: 376
<212> TYPE: PRT
<213> ORGANISM: Mus musculus

<400> SEQUENCE: 14
```

| | | | | | | | | | | | | | | |
|---|---|---|---|---|---|---|---|---|---|---|---|---|---|---|
| Met | Phe | Pro | Arg | Pro | Leu | Thr | Pro | Leu | Ala | Ala | Pro | Lys | Ser | Ala | Glu |
| 1 | | | | 5 | | | | | 10 | | | | | 15 | |

| Thr | Leu | Gly | Arg | Thr | Pro | Arg | Arg | Ala | Pro | Leu | Gly | Arg | Ala | Arg | Ala |
| | | | 20 | | | | | 25 | | | | | 30 | | |

| Gly | Leu | Gly | Gly | Pro | Pro | Leu | Leu | Leu | Pro | Ser | Met | Leu | Met | Phe | Ala |
| | | 35 | | | | | 40 | | | | | 45 | | | |

| Val | Ile | Val | Ala | Ser | Ser | Gly | Leu | Leu | Leu | Met | Ile | Glu | Arg | Gly | Ile |
| 50 | | | | | 55 | | | | | 60 | | | | | |

| Leu | Ser | Glu | Met | Lys | Pro | Leu | Pro | Leu | His | Pro | Ser | His | Lys | Gly |
| 65 | | | | 70 | | | | | 75 | | | | | 80 |

| Ala | Ala | Trp | Ser | Gly | Thr | Asp | Pro | Lys | Pro | Arg | Gly | Leu | Ser | Leu | Asp |
| | | | | 85 | | | | | 90 | | | | | 95 | |

| Ala | Gly | Asp | Ser | Asp | Leu | Gln | Val | Arg | Glu | Asp | Ile | Arg | Asn | Arg | Thr |
| | | | 100 | | | | | 105 | | | | | 110 | | |

| Leu | Arg | Ala | Val | Cys | Gly | Gln | Pro | Gly | Met | Pro | Arg | Asp | Pro | Trp | Asp |
| | | 115 | | | | | 120 | | | | | 125 | | | |

| Leu | Pro | Val | Gly | Gln | Arg | Arg | Thr | Leu | Leu | Arg | His | Ile | Leu | Val | Ser |
| | 130 | | | | | 135 | | | | | 140 | | | | |

| Asp | Arg | Tyr | Arg | Phe | Leu | Tyr | Cys | Tyr | Val | Pro | Lys | Val | Ala | Cys | Ser |
| 145 | | | | | 150 | | | | | 155 | | | | | 160 |

| Asn | Trp | Lys | Arg | Val | Leu | Lys | Val | Leu | Ala | Gly | Ile | Leu | Asn | Asn | Val |
| | | | | 165 | | | | | 170 | | | | | 175 | |

| Asp | Val | Arg | Leu | Lys | Met | Asp | His | Arg | Ser | Asp | Leu | Val | Phe | Leu | Ala |
| | | | 180 | | | | | 185 | | | | | 190 | | |

| Asp | Leu | Arg | Pro | Glu | Glu | Ile | Arg | Tyr | Arg | Leu | Gln | His | Tyr | Phe | Lys |
| | | 195 | | | | | 200 | | | | | 205 | | | |

| Phe | Leu | Phe | Val | Arg | Asp | Pro | Leu | Glu | Arg | Leu | Leu | Ser | Ala | Tyr | Arg |
| | 210 | | | | | 215 | | | | | 220 | | | | |

| Asn | Lys | Phe | Gly | Glu | Ile | Arg | Glu | Tyr | Gln | Gln | Arg | Tyr | Gly | Ala | Glu |
| 225 | | | | | 230 | | | | | 235 | | | | | 240 |

| Ile | Val | Arg | Arg | Tyr | Arg | Ala | Gly | Ala | Gly | Pro | Ser | Pro | Ala | Gly | Asp |
| | | | | 245 | | | | | 250 | | | | | 255 | |

| Asp | Val | Thr | Phe | Pro | Glu | Phe | Leu | Arg | Tyr | Leu | Val | Asp | Glu | Asp | Pro |
| | | | 260 | | | | | 265 | | | | | 270 | | |

| Glu | His | Met | Asn | Glu | His | Trp | Met | Pro | Val | Tyr | His | Leu | Cys | Gln | Pro |
| | | 275 | | | | | 280 | | | | | 285 | | | |

```
Cys Ala Val His Tyr Asp Phe Val Gly Ser Tyr Glu Arg Leu Glu Ala
            290                 295                 300
Asp Ala Asn Gln Val Leu Glu Trp Val Arg Ala Pro Pro His Val Arg
305                 310                 315                 320
Phe Pro Ala Arg Gln Ala Trp Tyr Arg Pro Ala Ser Pro Glu Ser Leu
                325                 330                 335
His Tyr His Leu Cys Asn Val Pro Arg Ala Leu Leu Gln Asp Val Leu
            340                 345                 350
Pro Lys Tyr Ile Leu Asp Phe Ser Leu Phe Ala Tyr Pro Leu Pro Asn
        355                 360                 365
Val Thr Lys Glu Ala Cys His Gln
370                 375
```

<210> SEQ ID NO 15
<211> LENGTH: 376
<212> TYPE: PRT
<213> ORGANISM: Homo sapiens

<400> SEQUENCE: 15

```
Met Phe Pro Arg Pro Leu Thr Pro Leu Ala Ala Pro Asn Gly Ala Glu
1               5                   10                  15
Pro Leu Gly Arg Ala Leu Arg Arg Ala Pro Leu Gly Arg Ala Arg Ala
                20                  25                  30
Gly Leu Gly Gly Pro Pro Leu Leu Leu Pro Ser Met Leu Met Phe Ala
            35                  40                  45
Val Ile Val Ala Ser Ser Gly Leu Leu Leu Met Ile Glu Arg Gly Ile
        50                  55                  60
Leu Ala Glu Met Lys Pro Leu Pro Leu His Pro Pro Gly Arg Glu Gly
65                  70                  75                  80
Thr Ala Trp Arg Gly Lys Ala Pro Lys Pro Gly Gly Leu Ser Leu Arg
                85                  90                  95
Ala Gly Asp Ala Asp Leu Gln Val Arg Gln Asp Val Arg Asn Arg Thr
            100                 105                 110
Leu Arg Ala Val Cys Gly Gln Pro Gly Met Pro Arg Asp Pro Trp Asp
        115                 120                 125
Leu Pro Val Gly Gln Arg Arg Thr Leu Leu Arg His Ile Leu Val Ser
130                 135                 140
Asp Arg Tyr Arg Phe Leu Tyr Cys Tyr Val Pro Lys Val Ala Cys Ser
145                 150                 155                 160
Asn Trp Lys Arg Val Met Lys Val Leu Ala Gly Val Leu Asp Ser Val
                165                 170                 175
Asp Val Arg Leu Lys Met Asp His Arg Ser Asp Leu Val Phe Leu Ala
            180                 185                 190
Asp Leu Arg Pro Glu Glu Ile Arg Tyr Arg Leu Gln His Tyr Phe Lys
        195                 200                 205
Phe Leu Phe Val Arg Glu Pro Leu Glu Arg Leu Leu Ser Ala Tyr Arg
210                 215                 220
Asn Lys Phe Gly Glu Ile Arg Glu Tyr Gln Gln Arg Tyr Gly Ala Glu
225                 230                 235                 240
Ile Val Arg Arg Tyr Arg Ala Gly Ala Gly Pro Ser Pro Ala Gly Asp
                245                 250                 255
Asp Val Thr Phe Pro Glu Phe Leu Arg Tyr Leu Val Asp Glu Asp Pro
            260                 265                 270
Glu Arg Met Asn Glu His Trp Met Pro Val Tyr His Leu Cys Gln Pro
        275                 280                 285
```

```
Cys Ala Val His Tyr Asp Phe Val Gly Ser Tyr Glu Arg Leu Glu Ala
        290                 295                 300

Asp Ala Asn Gln Val Leu Glu Trp Val Arg Ala Pro Pro His Val Arg
305                 310                 315                 320

Phe Pro Ala Arg Gln Ala Trp Tyr Arg Pro Ala Ser Pro Glu Ser Leu
                325                 330                 335

His Tyr His Leu Cys Ser Ala Pro Arg Ala Leu Leu Gln Asp Val Leu
            340                 345                 350

Pro Lys Tyr Ile Leu Asp Phe Ser Leu Phe Ala Tyr Pro Leu Pro Asn
        355                 360                 365

Val Thr Lys Glu Ala Cys Gln Gln
        370                 375

<210> SEQ ID NO 16
<211> LENGTH: 367
<212> TYPE: PRT
<213> ORGANISM: Danio rerio

<400> SEQUENCE: 16

Met Pro Pro Arg Lys Lys Glu Tyr Gly Ile Lys Arg Ala Ser Gly Ser
1               5                   10                  15

Leu Val His Phe Arg Ala Pro Val Ser Ala Thr Thr Ile Arg Arg His
            20                  25                  30

Ser Ala Val Val Pro Ser Val Leu Thr Phe Ala Val Ile Val Ala Ser
        35                  40                  45

Gly Gly Leu Leu Leu Met Ile Glu Lys Gly Met Leu Asn Ser Val Gln
    50                  55                  60

Thr Pro Pro Pro Arg Ala Asn Gly Arg Lys Val Glu Tyr Arg Leu Arg
65                  70                  75                  80

Ser Ser Ser Asp Thr Ala Ala Asp Val Glu Ser Gln Ile Val Gln Glu
                85                  90                  95

Ile Arg Asn Arg Thr Ile Arg Ser Val Cys Gly Gln Arg Asn Met Pro
            100                 105                 110

His Ser Val Trp Ser Leu Ser Pro Leu Gln Arg Lys Thr Leu Leu Gln
        115                 120                 125

His Ile Leu Val Asn Asp Glu His Arg Phe Leu Tyr Cys Tyr Val Pro
    130                 135                 140

Lys Val Ala Cys Ser Asn Trp Lys Arg Val Leu Lys Val Leu Ser Gly
145                 150                 155                 160

Ala Leu Ala Asn Val Asp Ile Lys Val Lys Met Asp His Arg Ala Asp
                165                 170                 175

Leu Val Phe Leu Ser Asp Leu Pro Pro Glu Glu Ile Arg His Arg Leu
            180                 185                 190

Arg His Tyr Phe Lys Phe Met Phe Val Arg Glu Pro Met Ala Arg Leu
        195                 200                 205

Leu Ser Ala Tyr Arg Asn Lys Phe Gly Glu Ile Glu Ala Tyr Gln Arg
    210                 215                 220

Lys Tyr Gly Ala Glu Ile Ile Arg Arg Tyr Arg Lys Gly Tyr Ala Lys
225                 230                 235                 240

Asp Lys Lys Ile Ser Gly Asn Asp Val Thr Phe Thr Glu Phe Thr Arg
                245                 250                 255

Tyr Leu Val Asp Glu Asp Pro Glu Arg Met Asn Glu His Trp Met Pro
            260                 265                 270

Ile Tyr Asn Leu Cys Gln Pro Cys Ala Ile Glu Tyr Asp Phe Ile Gly
```

-continued

```
                275                 280                 285
Ser Tyr Glu Arg Leu Glu Ser Asp Ala Ser Tyr Ile Leu Glu Arg Val
        290                 295                 300

Gly Ala Pro Gln His Val Arg Phe Pro Glu Arg Gln Thr Trp Tyr Lys
305                 310                 315                 320

Pro Val Thr Lys Glu Thr Leu His Tyr Tyr Leu Cys Thr Val Pro Gln
                325                 330                 335

Lys Phe Leu Lys Glu Leu Leu Pro Lys Tyr Ile Leu Asp Phe Ser Leu
                340                 345                 350

Phe Gly Tyr Pro Leu Pro Asn Thr Thr Thr Glu Tyr Cys Arg His
                355                 360                 365
```